United States Patent
Schena et al.

(12)

(10) Patent No.: US 7,909,122 B2
(45) Date of Patent: Mar. 22, 2011

(54) METHODS OF STEERING HEAVY MOBILE MEDICAL EQUIPMENT

(75) Inventors: Bruce M. Schena, Menlo Park, CA (US); Henry B. Hazebrouck, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 12/420,222

(22) Filed: Apr. 8, 2009

(65) Prior Publication Data

US 2009/0200092 A1    Aug. 13, 2009

Related U.S. Application Data

(63) Continuation of application No. 11/536,640, filed on Sep. 28, 2006, now Pat. No. 7,533,892.

(60) Provisional application No. 60/756,440, filed on Jan. 5, 2006.

(51) Int. Cl.
*B62D 3/00* (2006.01)
*B62D 51/04* (2006.01)

(52) U.S. Cl. ....... 180/19.1; 280/47.11; 280/98; 280/103

(58) Field of Classification Search ................ 180/19.1; 280/47.11, 98, 103

See application file for complete search history.

(56) References Cited

U.S. PATENT DOCUMENTS

| | | | |
|---|---|---|---|
| 2,834,605 A | 5/1958 | Mccollough | |
| 3,028,172 A | 4/1962 | Herbenar | |
| 3,299,247 A | 1/1967 | Waltonen | |
| 4,301,882 A * | 11/1981 | Dera et al. | 180/433 |
| 5,090,512 A | 2/1992 | Mullet et al. | |
| 5,529,316 A | 6/1996 | Mattila | |
| 5,862,874 A | 1/1999 | Brienza et al. | |
| 6,016,580 A * | 1/2000 | Heimbrock et al. | 5/86.1 |
| 6,246,200 B1 * | 6/2001 | Blumenkranz et al. | 318/568.11 |
| 6,672,411 B1 | 1/2004 | Mouser | |
| 6,793,036 B1 | 9/2004 | Enmeiji et al. | |
| 6,921,109 B2 | 7/2005 | Hutchison et al. | |

(Continued)

FOREIGN PATENT DOCUMENTS

EP    541868 A1    5/1993

OTHER PUBLICATIONS

U.S. Appl. No. 11/536,640 Office Action mailed Jul. 24, 2008, 16 pages.

(Continued)

*Primary Examiner* — Joanne Silbermann
*Assistant Examiner* — Jacob Knutson

(57) ABSTRACT

Methods for steering mobile medical equipment are disclosed. In one embodiment, the method includes supporting medical equipment with a base above a floor over which a left steerable wheel, a right steerable wheel, and a pair of front wheels roll; receiving an input steering angle other than zero; linearly sweeping a long link in response to the input steering angle, pivoting a pair of short links in response to the linearly sweeping of the long link; pivoting a pair of cam plates in response to the pivoting of the pair of short links; transferring the pivoting of one of the pair of cam plates to a left wheel assembly to position the left steerable wheel at a left wheel angle; and transferring the pivoting of another one of the pair of cam plates to a right wheel assembly to position the right steerable wheel at a right wheel angle.

17 Claims, 18 Drawing Sheets

U.S. PATENT DOCUMENTS

| | | | |
|---|---|---|---|
| 6,938,711 B2 * | 9/2005 | Kime et al. | 180/11 |
| 7,063,633 B2 | 6/2006 | Robert | |
| 7,073,613 B2 | 7/2006 | Wakitani et al. | |
| 7,125,403 B2 | 10/2006 | Julian et al. | |
| 7,192,040 B2 | 3/2007 | Xie | |
| 7,383,112 B2 | 6/2008 | Shin et al. | |
| 7,401,794 B2 | 7/2008 | Laurent et al. | |
| 7,407,024 B2 | 8/2008 | Vogel et al. | |
| 7,429,019 B1 | 9/2008 | Bietenhader | |
| 7,431,325 B2 | 10/2008 | Stähle | |
| 2006/0213698 A1 | 9/2006 | Gaetani | |

OTHER PUBLICATIONS

Autoware, Inc., "Ackerman Steering and Racing Oval Tracks," 1998, 1 page, Internet http://www.auto-ware.com/setup/ack_rac.htm.

Barnes, George, "Ackerman Steering," National T-Bucket Alliance web site, 3 pages, 2002, Internet http://www.nationaltbucketalliance.com/tech_info/chassis/ackerman/Ackerman.asp.

Crouse, William H., Automotive Mechanics, 6th Edition, McGraw Hill, USA, vol. 7, Chapter 38, pp. 478-497, 1970.

RCTEK, "Model Car Handling—Ackerman Steering Principle," 5 Pages, 2000/2001, Internet http://www.rctek.com/handling/ackerman_steering_principle.html.

Tolboldt, William K. and Larry Johnson, Motor Service's Automotive Encyclopedia, Goodheart-Wilcox Co., Chicago, 1978 or prior, pp. 479-491.

Vertut, Jean et al., Robot Technology: Teleoperation and Robotics Evolution and Development, 1986, vol. 3A, 332 pages, English translation Prentice-Hall, Inc., Inglewood Cliffs, NJ, USA.

* cited by examiner

METHODS OF STEERING HEAVY MOBILE MEDICAL EQUIPMENT

CROSS-REFERENCE TO RELATED APPLICATIONS

This non-provisional U.S. patent application is a continuation and claims the benefit of U.S. patent application Ser. No. 11/536,640 entitled "STEERING SYSTEM FOR MOBILE MEDICAL EQUIPMENT" filed on Sep. 28, 2006 by inventors Bruce M Schena and Henry Hazebrouck which is incorporated herein by reference in its entirety. U.S. patent application Ser. No. 11/536,640 claims the benefit of U.S. Provisional Patent Application No. 60/756,440 entitled "STEERING SYSTEM FOR MOBILE MEDICAL EQUIPMENT" filed on Jan. 5, 2006 by inventors Bruce M Schena and Henry Hazebrouck which is incorporated herein by reference in its entirety.

FIELD

The embodiments of the invention relate generally to mobile carts for medical equipment. More particularly, the embodiments of the invention relate to steering systems for mobile robotic surgical systems.

BACKGROUND

Typical robotic surgical systems are very expensive. To make the investment more attractive to hospitals and surgical centers, it is desirable to make the robotic surgical system mobile so that it can be moved from room to room such that it is more efficiently used. To effectively move a mobile robotic surgical system, a steering system may be required.

One type of steering system that may be used is an Ackerman steering system that is commonly found in cars and trucks. However, the typical Ackerman steering linkage works appropriately when the turning radius is quite large. The typical Ackerman steering linkage does not work well in vehicles with a small turning radius where high mobility is desirable.

It is desirable to provide a steering system for heavy medical equipment, such as may be found in a robotic surgical system, that operates with a small turning radius to provide a highly mobile medical equipment system.

BRIEF SUMMARY

The embodiments of the invention are summarized by the claims that follow below.

BRIEF DESCRIPTIONS OF THE DRAWINGS

Figure 1A:
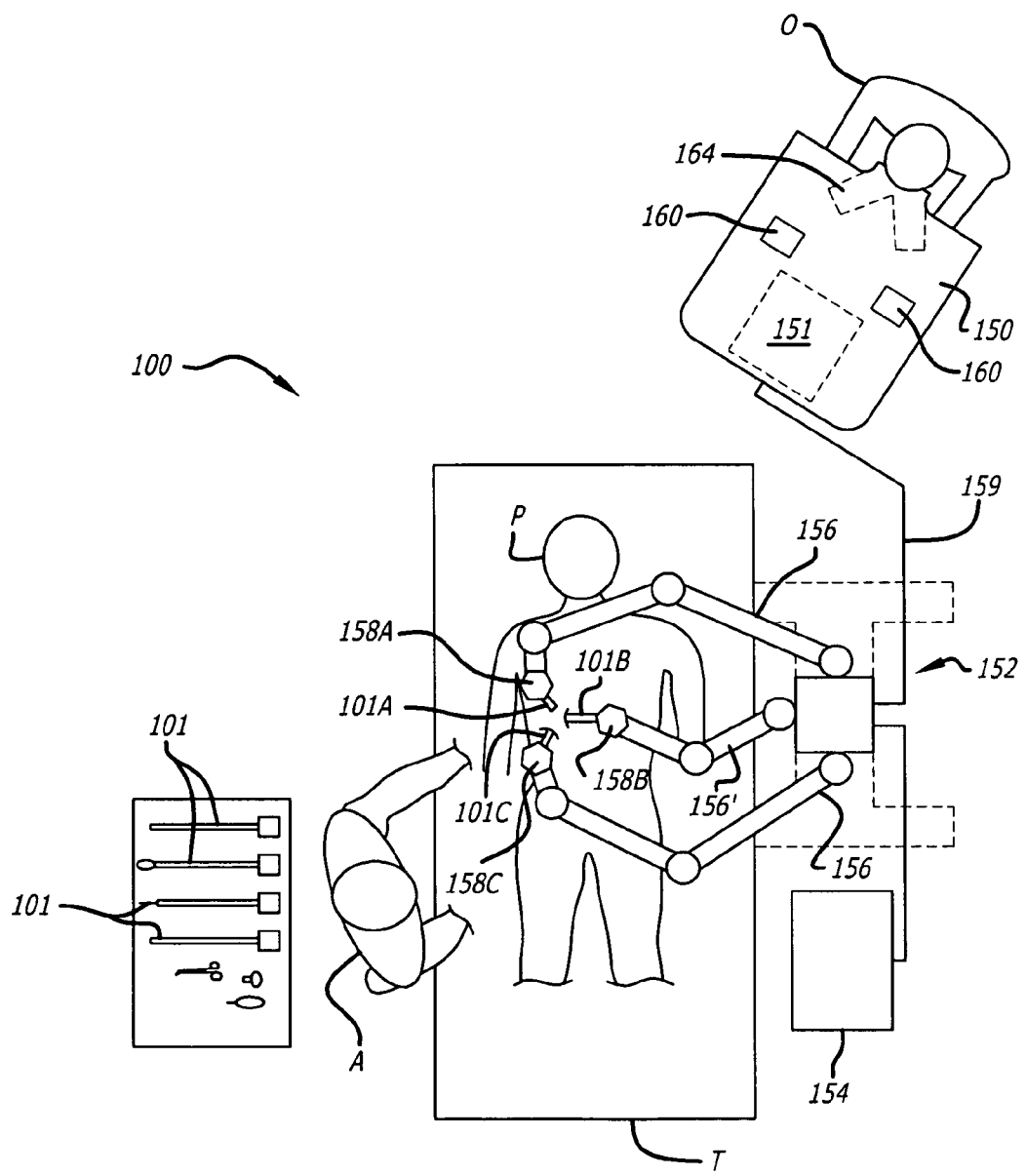
FIG. 1A is a block diagram of a robotic surgery system to perform minimally invasive robotic surgical procedures using one or more robotic surgical arms.

It will be appreciated that all the drawings of figures provided for herein are for illustrative purposes only and do not necessarily reflect the actual shape, size, or dimensions of the elements being illustrated.

DETAILED DESCRIPTION

In the following detailed description of the embodiments of the invention, numerous specific details are set forth in order to provide a thorough understanding of the present invention. However, it will be obvious to one skilled in the art that the embodiments of the invention may be practiced without these specific details. In other instances well known methods, procedures, components, and circuits have not been described in detail so as not to unnecessarily obscure aspects of the embodiments of the invention.

The embodiments of the invention include methods, apparatus and systems for a steering system for heavy mobile medical equipment.

In one embodiment of the invention, a mobile medical equipment system is disclosed including a mobile base to movably support medical equipment, the mobile base having a chassis having a left side, a right side, a front side, and a back side; a pair of motorized wheels rotatably coupled to the chassis near the front and the left and right sides, the pair of motorized wheels to drive the mobile medical equipment system over a floor; a left steerable wheel and a right steerable wheel pivotally coupled to the chassis near the back side and the left side and right side respectively, the left and right steerable wheels to steer the mobile medical equipment system around the floor; a tiller coupled to the chassis near the back, the tiller to receive directional input from a user; and a steering system coupled to the chassis and the left and right steerable wheels, the steering system including a pair of cam followers in a pair of cam follower slots to convert directional input from the tiller to the left and right steerable wheels.

In another embodiment of the invention, a method for steering mobile medical equipment having four wheels is disclosed including generating a left wheel angle and a right wheel angle in response to an input steering angle other than zero, the right wheel angle differing from the left wheel angle; transferring the left wheel angle to a left wheel assembly to position a left steerable wheel; transferring the right wheel angle to a right wheel assembly to position a right steerable wheel; and wherein the position of the right steerable wheel differs from the position of the left steerable wheel, and the different positions of the right steerable wheel and the left steerable wheel steer the mobile medical equipment over a floor.

In another embodiment of the invention, a steering system for mobile medical equipment is disclosed including a left steerable wheel assembly including a left steerable wheel; a right steerable wheel assembly including a right steerable wheel; a left parallelogram linkage coupled to the left steerable wheel assembly, the left parallelogram linkage to transfer a left wheel angle to the left steerable wheel assembly; a right parallelogram linkage coupled to the right steerable wheel assembly, the right parallelogram linkage to transfer a right wheel angle to the right steerable wheel assembly; a steering function generator coupled to the left parallelogram linkage and the right parallelogram linkage, the steering function generator to generate the left wheel angle (LWA) of the left steerable wheel and the right wheel angle (RWA) of the right steerable wheel; and a steering tiller coupled to the steering function generator, the steering tiller to receive an input steering angle from an equipment operator EO to generate the left wheel angle and the right wheel angle to control the direction of the mobile medical equipment around flooring.

In another embodiment of the invention, a method for steering mobile medical equipment having four wheels is disclosed including receiving an input steering angle other than zero and generating a pivotal motion in a first link, converting the pivotal motion of the first link into a linear sweeping motion of a second link; converting the linear sweeping motion of the second link into a pivotal motion of a third link and a fourth link, the fourth link spaced apart from the third link; unequally transferring the pivotal motion of the third link and the fourth link respectively into a first parallelogram linkage and a second parallelogram linkage; transferring the pivotal motion in the first parallelogram linkage to a first wheel assembly to form a first wheel angle, and transferring the pivotal motion in the second parallelogram linkage to a second wheel assembly to form a second wheel angle, wherein the first wheel angle differs from the second wheel angle in response to the unequal transfer of the pivotal motion.

Robotic Surgical System

Referring now to FIG. 1A, a block diagram of a robotic surgery system 100 is illustrated to perform minimally invasive robotic surgical procedures using one or more robotic arms with strap drive. Robotic surgery generally involves the use of a robot manipulator that has multiple robotic manipulator arms. One or more of the robotic manipulator arms often support a surgical tool which may be articulated (such as jaws, scissors, graspers, needle holders, micro dissectors, staple appliers, tackers, suction/irrigation tools, clip appliers, or the like) or non-articulated (such as cutting blades, cautery probes, irrigators, catheters, suction orifices, or the like). At least one of the robotic manipulator arms (e.g., the center robotic manipulator arm 158B) is used to support a stereo or three dimensional surgical image capture device 110 such as a stereo endoscope (which may be any of a variety of structures such as a stereo laparoscope, arthroscope, hysteroscope, or the like), or, optionally, some other stereo imaging modality (such as ultrasound, fluoroscopy, magnetic resonance imaging, or the like). Robotic surgery may be used to perform a wide variety of surgical procedures, including but not limited to open surgery, neurosurgical procedures (such as stereotaxy), endoscopic procedures (such as laparoscopy, arthroscopy, thoracoscopy), and the like.

A user or operator O (generally a surgeon) performs a minimally invasive surgical procedure on patient P by manipulating control input devices 160 at a master control console 150. A computer 151 of the console 150 directs movement of robotically controlled endoscopic surgical instruments 101A-101C by means of one or more control cables 159, effecting movement of the instruments using a robotic patient-side surgery system 152 that is also referred to as a patient-side cart (PSC). The robotic patient-side surgery system 152 has one or more robotic arms 158. In a preferred embodiment of the invention, the one or more robotic arms 158 have a strap drive system. Typically, the robotic patient-side surgery system 152 includes at least three robotic manipulator arms 158A-158C supported by linkages 156, 156', with a central robotic arm 158B supporting an endoscopic camera 101B and the robotic arms 158A, 158C to left and right of center supporting tissue manipulation tools 101A and 101C.

Generally, the robotic patient-side surgery system 152 includes a positioning portion and a driven portion. The positioning portion of the robotic patient-side surgery system 152 remains in a fixed configuration during surgery while manipulating tissue. The driven portion of the robotic patient-side surgery system 152 is actively articulated under the direction of the operator O generating control signals at the surgeon's console 150 during surgery. The actively driven portion of the robotic patient-side system surgery 152 is generally referred to herein as the robotic arms or alternatively to robotic surgical manipulators. The positioning portion of the robotic patient-side surgery system 152 that is in a fixed configuration during surgery may be referred to as "set up arms" 156, 156' with positioning linkage and/or "set-up joints" (SUJ). In an alternate embodiment of the invention, the robotic patient-side surgery system 152 may be replaced by set up arms that couple at one end to left and right sides of the operating table T. The three robotic manipulator arms 158A-158C may then be coupled to the opposite end of the set-up arms to ground to the table T.

For convenience in terminology, manipulators such as robotic surgical arms 158A and 158C actuating the tissue affecting surgical tools 101A and 101C are generally referred to herein as a PSM (patient-side manipulators), and a robotic surgical arm 158B controlling an image capture or data acquisition device, such as the endoscopic camera 101B, is generally referred to herein as a ECM (endoscope-camera manipulator), it being noted that such telesurgical robotic manipulators may optionally actuate, maneuver and control a wide variety of instruments, tools and devices useful in surgery. The surgical tools 101A, 101C and endoscopic camera 101B may be generally referred to herein as tools or instruments 101.

An assistant A may assist in pre-positioning of the robotic patient-side surgery system 152 relative to patient P as well as swapping tools or instruments 101 for alternative tool structures and the like, while viewing the internal surgical site via an assistant's display 154. With the embodiments of the invention, the assistant A may also swap in and out the robotic surgical arms 158A and 158C, as well as the robotic surgical arm 158B, in case one is defective or failing. In other cases, a robotic surgical arm may be swapped out for maintenance, adjustments, or cleaning and then swapped back in by one or more service persons.

Figure 1B:
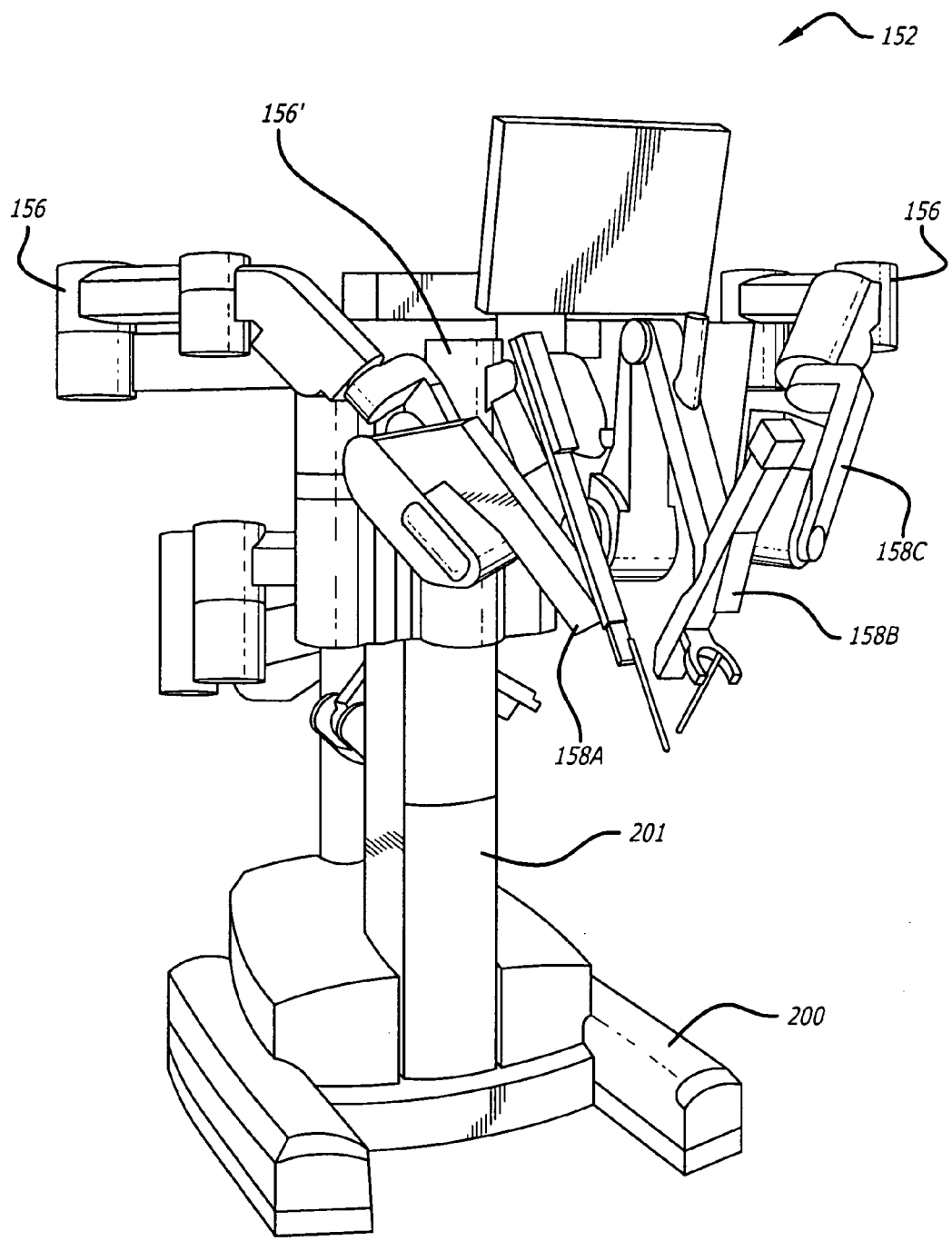
FIG. 1B is a perspective view of the robotic patient-side system of FIG. 1A with the one or more robotic surgical arms coupled thereto.

Referring now to FIG. 1B, a perspective view of the robotic patient-side system 152 is illustrated. The robotic patient-side surgery system 152 may have one or more robotic surgical arms (a.k.a., robotic surgical manipulators) 158A-158C with a strap drive system to manipulate the arm and any robotic surgical tool coupled there-to. The robotic arms 158A, 158C are for coupling to robotic surgical tools 101A, 101C. The robotic arm 158B is for coupling to an endoscopic camera 101B. Generally, the surgical robotic arms 158A-158C may be referred to as a surgical robotic arm or a robotic surgical arm 158.

The robotic patient-side surgery system 152 further includes a mobile base 200 from which the robotic surgical instruments 101 may be supported. More specifically, the robotic surgical instruments 101 are each supported by the positioning linkage 156 and the surgical robotic arms 158. The linkage structures may optionally be covered by protective covers or not to minimize the inertia that is manipulated by the servomechanism and the overall weight of robotic patient-side surgery system 152.

The robotic patient-side surgery system 152, an exemplary mobile medical equipment system, is designed to be rolled around the hospital corridors and within the operating room. The robotic patient-side surgery system 152 generally has dimensions suitable for transporting between operating rooms. It typically can fit through standard operating room doors and onto standard hospital elevators. The robotic patient-side surgery system 152 may have a weight and a wheel (or other transportation) system that allows the cart to be positioned adjacent to an operating table by a single attendant. The robotic patient-side surgery system 152 may be sufficiently stable during transport to avoid tipping and to easily withstand overturning moments that may be imposed at the ends of the robotic arms during use. The robotic patient-side surgery system 152 weighs approximately one-thousand two-hundred pounds in one embodiment of the invention. The robotic patient-side surgery system 152, including the robotic arms 158, set up arms, and the mobile base 200, is also referred to herein as the "Patient Side Cart" or PSC 152.

Mobile Base

Figure 2A:
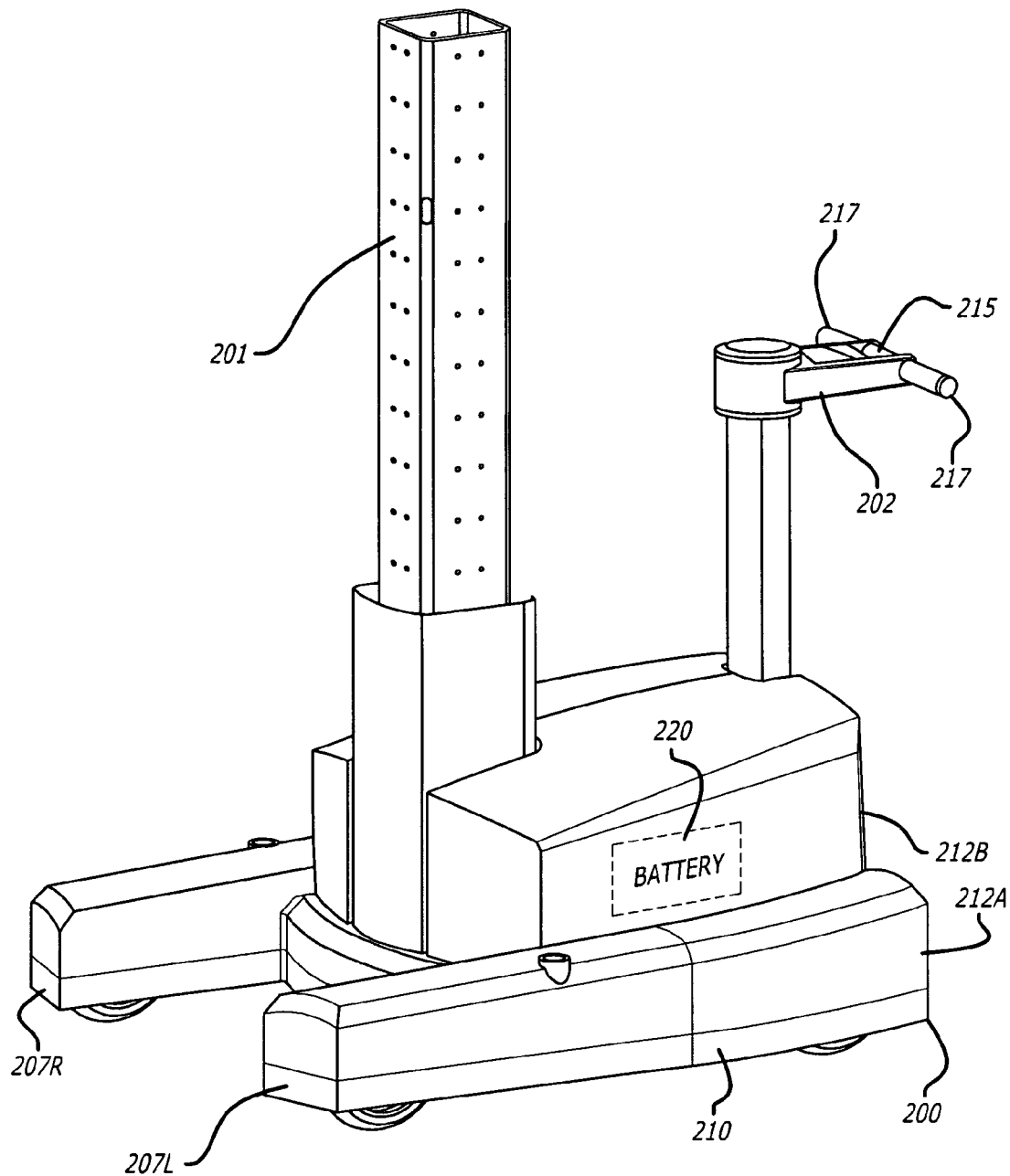
FIG. 2A is a perspective side view of a mobile base for the robotic patient side system of FIG. 1B.

Referring now to FIG. 2A, a perspective side view of the mobile base 200 is illustrated without any robotic arms or any set up arms coupled there-to in order to better illustrate the elements of the base 200. However, the robotic patient-side surgery system 152 typically includes the setup arms 156, the set up joints 156', and a plurality of robotic surgical arms 158A, 158B, 158C.

The mobile base 200 includes a tiller 202 to steer and move the robotic patient-side surgery system 152 around hospital corridors and operating rooms. The tiller 202 may alternatively be referred to as a steering wheel. The mobile base 200 further includes a column 201 to which a set up arm can moveably couple to support a robotic surgical arm 158 over a patient. FIG. 1B illustrates the column 201 supporting a plurality of robotic surgical arms 158A, 158B, 158C by way of the setup arms 156 and set up joints 156'. It is to be understood that a reference to the mobile base 200 herein is also a reference to the robotic patient-side surgery system 152 including the set up arms and set up joints.

Figure 2B:
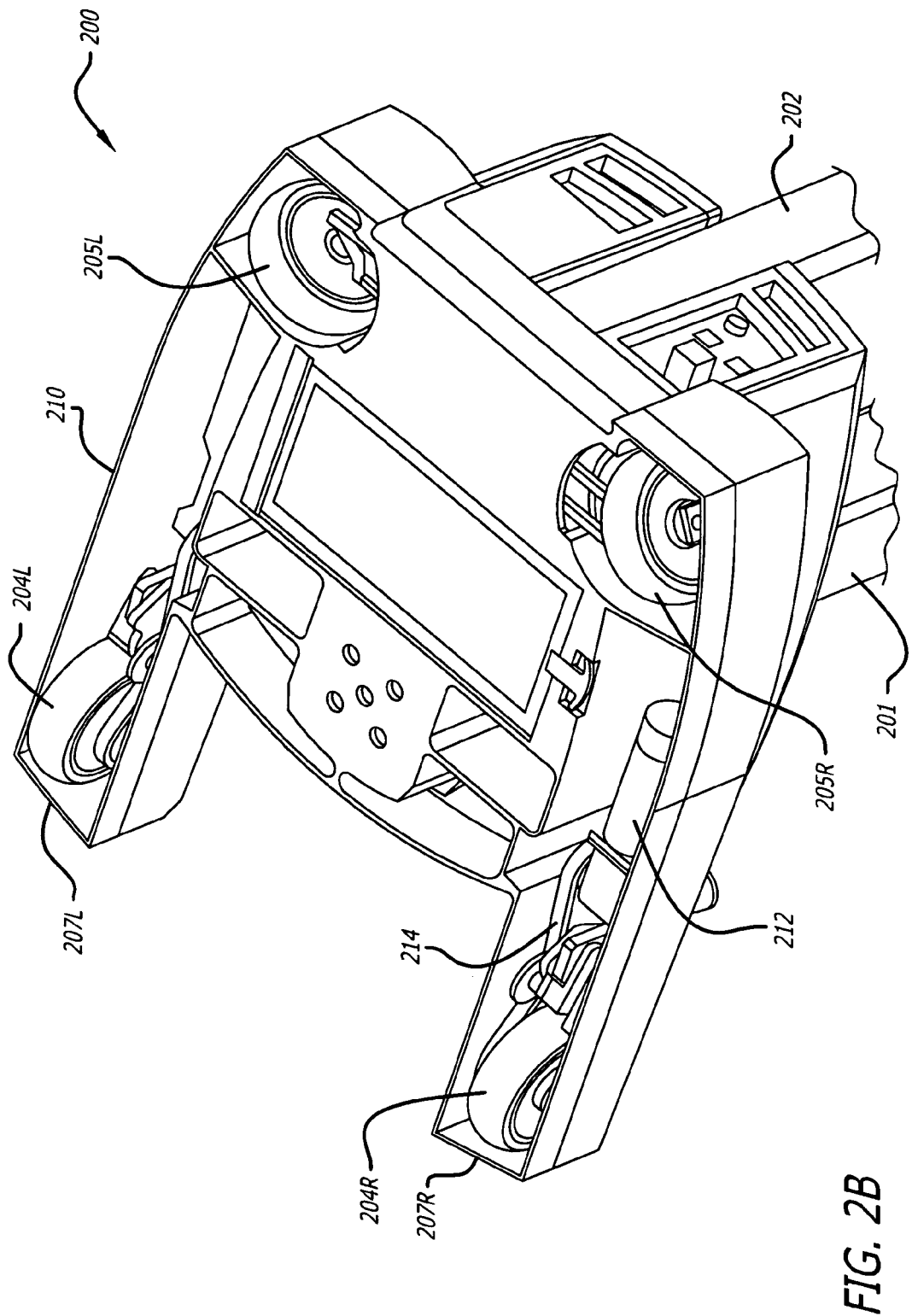
FIG. 2B is a bottom view of the mobile base illustrated in FIG. 2A.

Referring now to FIG. 2B, the mobile base 200 of the robotic patient-side surgery system 152 further has four wheels 204R,204L,205R,205L. In order to maximize mobility of the PSC 152 in the vicinity of an operating room table, a "front-wheel-drive, rear-wheel-steer" (e.g. forklift-like) system was chosen. The two front wheels 204R,204L may be motorized wheels and in a fixed orientation relative to the mobile base 200 in one embodiment of the invention. In another embodiment of the invention, the two front wheels 204R,204L are rotatably coupled to the chassis in a fixed orientation relative to the mobile base 200 but are not motorized. In either case, the two front wheels 204R,204L are non-steerable and can roll the mobile base over a floor.

The two rear wheels 205R,205L are non-motorized but are steerable wheels that can be steered by the tiller 202 to turn the mobile base 200.

This front-wheel-drive, rear-wheel-steer" (e.g. forklift-like) system provides significant design advantages as well— the motorized wheels 204R,204L are nicely packaged in the front "pontoons" 207R,207L while more space could be provided toward the rear of the mobile base 200 for the steering mechanism and "swing room" for the two rear wheels 205R, 205L and their respective steerable wheel assemblies.

The mobile base 200 further has a cast chassis 210 to support the robotic patient-side surgery system 152 on the motorized wheels 204R,204L and the two rear steerable wheels 205R,205L. The cast chassis 210 receives the motorized wheel assemblies and the steerable wheel assemblies for the wheels 204R,204L and 205R,205L, respectively. The mobile base 200 further has enclosure covers 212A,212B to cover over the motorized wheel assemblies and the steerable wheel assemblies coupled to the chassis 210.

Each of the motorized wheel assemblies includes a motorized wheel 204L,204R, a motor 212, and a chain drive 214 coupled together and mounted in a pontoon 207L,207R of the chassis 210. Each of the motors 212 in the pontoons 207L, 207R are controlled by a variable speed control switch 215 that is readily accessible to a user near the handles 217 of the tiller 202.

Figure 3:
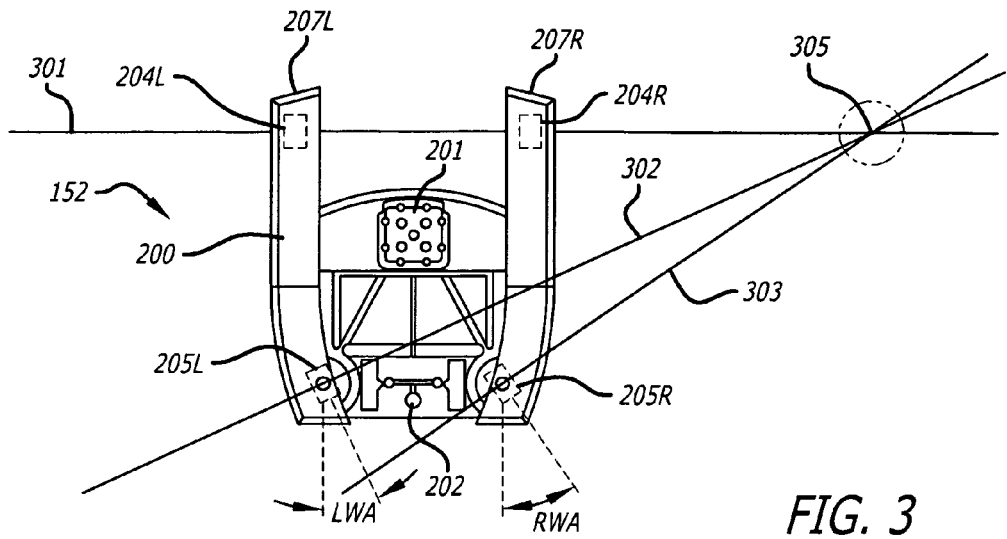
FIG. 3 is a diagram illustrating a top view of the mobile base with lines of axes through axles of the wheels of the mobile base.

Referring now to FIG. 3, a top view of the mobile base 200 with lines of axes 301-303 drawn through wheel axles to a center of turn 305. Line of axis 301 represents the fixed front wheel axis around which the motorized wheels 204L,204R rotate. That is, the motorized wheels 204L,204R are perpendicular to the axis 301. Line of axis 302 represents the steerable left wheel axis around which the left rear steerable wheel 205L rotates. That is, the left rear steerable wheel 205L is perpendicular to the axis 302. Line of axis 303 represents the steerable right wheel axis around which the right rear steerable wheel 205R rotates. That is, the right rear steerable wheel 205R is perpendicular to the axis 303. As illustrated in FIG. 3, lines 301-303 substantially intersect at the center of turn 305 about which the mobile base 200 can rotate. The center of turn 305 may also be referred to herein as a center of turning, a center turn point or an instant center. Note that the axes 301-303 may not perfectly intersect at the center of turn 305 due to compromises/tradeoffs made in the design of the steering system as well as due to manufacturing imperfections in the components and wear in the steering system as it is used over time.

FIG. 3 illustrates how the basic principles of Ackerman steering are applied to the robotic patient-side surgery system 152. A key requirement of any good steering system for a four-wheel vehicle is that the axis 301-303 defined by the rotation of each wheel (e.g. axle) should substantially intersect (ideally) at a single center turn point 305 (also referred to as the "center of turn", "center of turning" or "instant center"). Since the front wheels 204L,204R of the PSC 152 are fixed (e.g. non-steerable), the axes 302-303 drawn from each of the two (rear) steerable wheels 205L,205R substantially intersect near the same point somewhere along the fixed, front-wheel axis 301. While an Ackerman Linkage works well with in cars and trucks where the turning radius is quite large, it does not work well for high mobility, small turning radius vehicles.

As illustrated in FIGS. 2A-2B and 3, an equipment operator EO operates the mobile base 200 at its rear by turning the tiller 202 to move the steering mechanism that rotates the two (rear) steerable wheels 205L,205R. The operator EO further controls the forward and rearward motion of the mobile base 200 by the variable speed control switch 215 controlling the power supplied from the rechargeable batteries 220 to each motor 212 driving the motorized wheels 204L,204R.

Figure 8:
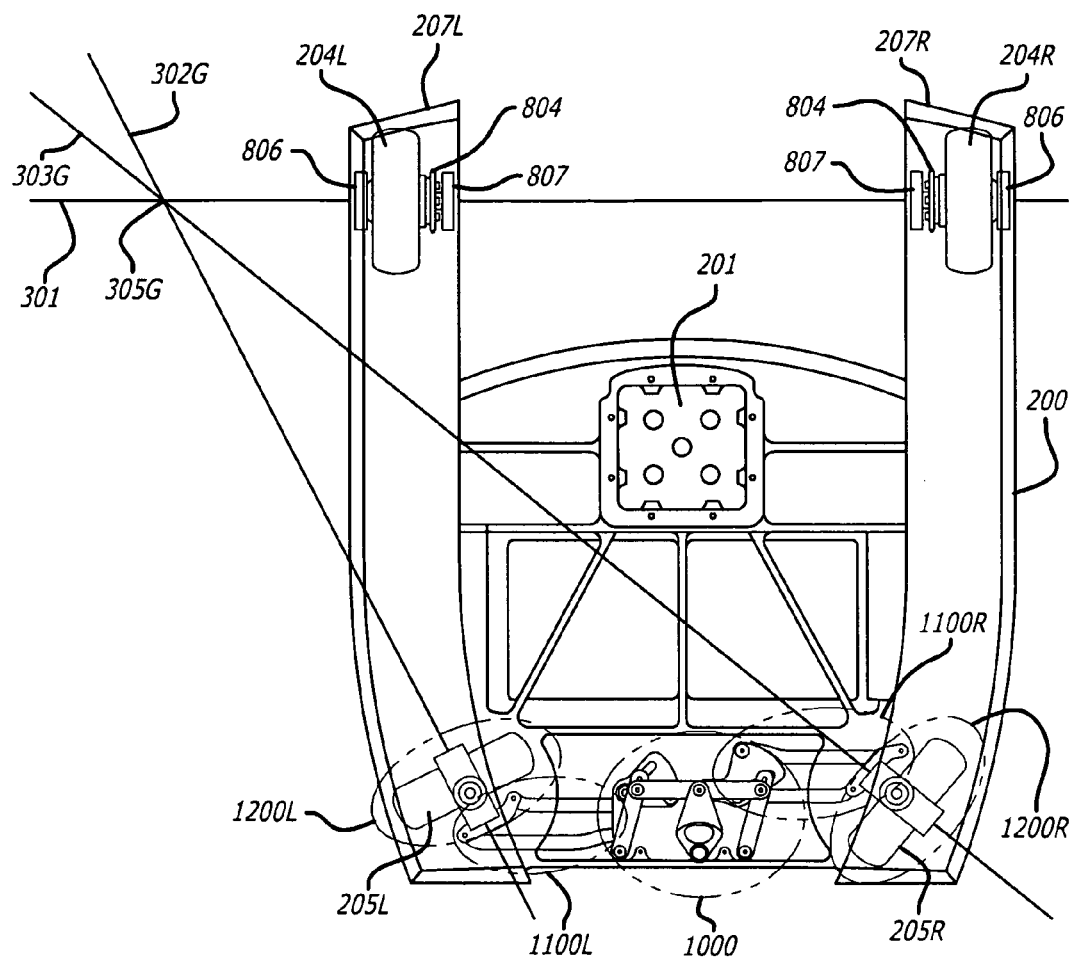
FIG. 8 illustrates a top cutaway view of the mobile base without the steering tiller subassembly to better illustrate subassemblies of the steering system of the patient side cart.

Referring now to FIGS. 4A-4E, a series of diagrams illustrate the desired steering linkage behavior for right turns of the mobile base 200 and PSC 152. The desired steering linkage behavior for left turns of the mobile base 200 and PSC 152 are simply mirror images of FIGS. 4B-4E. FIG. 8 illustrates one diagram of the position of the steering linkage for a left turn of the mobile base 200 and PSC 152.

Figure 4A:
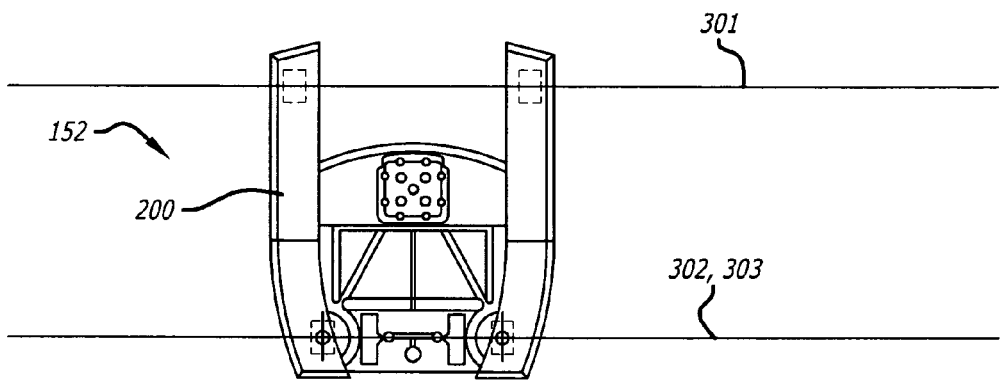
FIGS. 4A-4E are series of diagrams illustrating the desired steering linkage behavior for right turns of the mobile base and patient side cart.

In FIG. 4A, the PSC 152 is moving straight forward. The steerable wheels 205L,205R are pointed straight and parallel to each other (steerable wheels 205L,205R are "centered") to move the mobile base 200 straight forward. As a result, the axes 302,303 substantially intersect the axis 301 at infinity so that the mobile base 200 has an infinite turning radius.

Figure 4B:
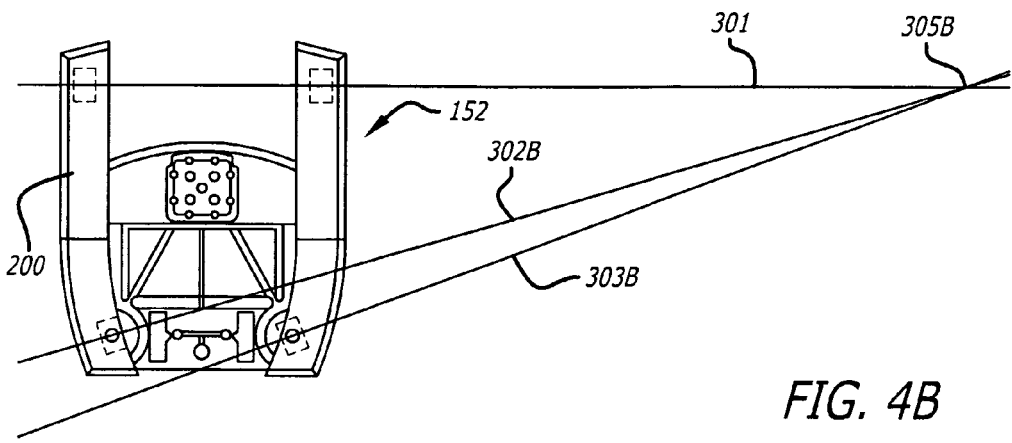

In FIG. 4B, the PSC 152 is executing a large-radius sweeping turn. The steerable wheels 205L,205R are pointed slightly to the left so that the axes 301, 302B, 303B substantially intersect a long distance away from the mobile base 200 at the center turn point 305B.

Figure 4C:
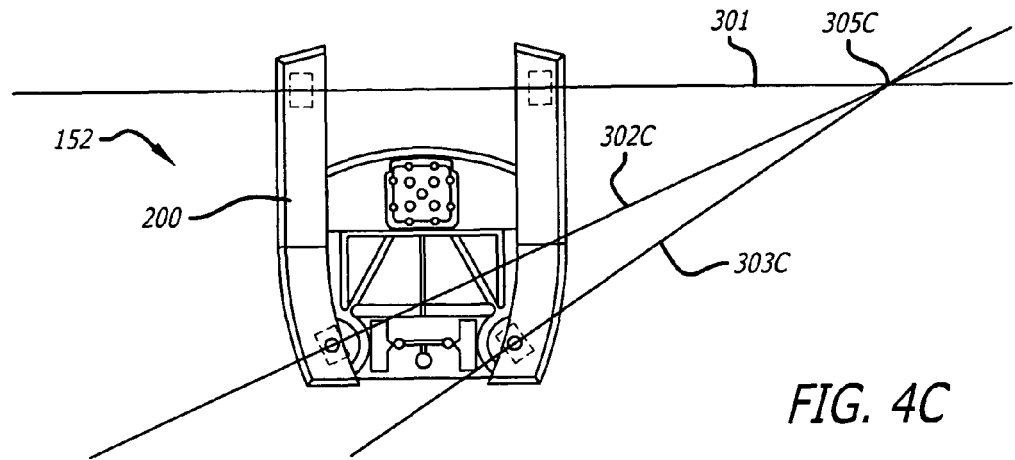

In FIG. 4C, the PSC 152 is executing a medium radius turn. The steerable wheels 205L,205R are pointed to the left so that the axes 301, 302C, 303C substantially intersect at the center turn point 305C.

Figure 4D:
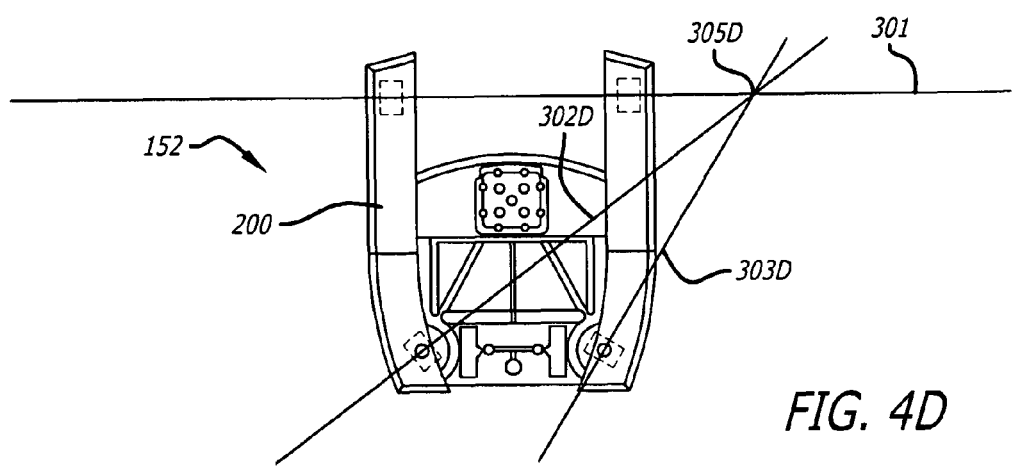

In FIG. 4D, the PSC 152 is executing a tight radius turn. The steerable wheels 205L,205R are pointed to the left so that the axes 301, 302D, 303D substantially intersect at the center turn point 305D.

Figure 4E:
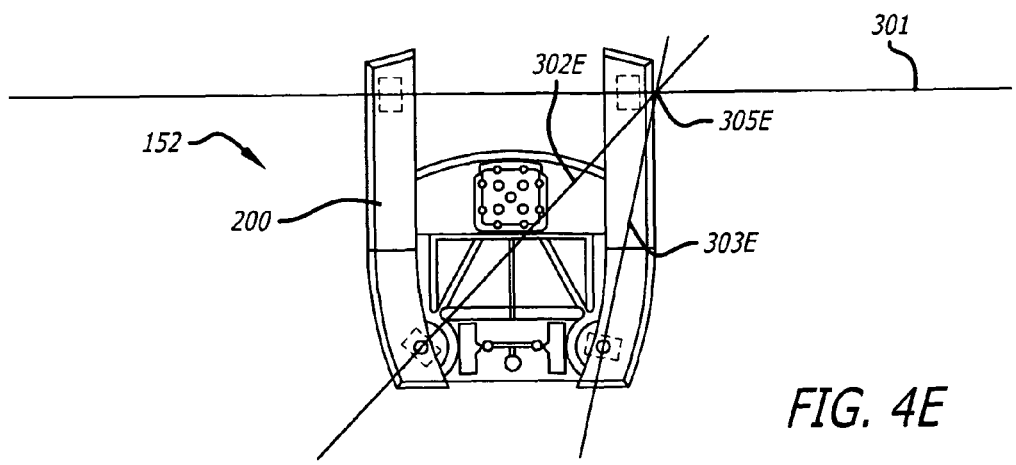

In FIG. 4E, the PSC 152 is executing a very tight radius turn. The steerable wheels 205L,205R are pointed more sharply to the left so that the axes 301, 302E, 303E substantially intersect just at the outer edge of the PSC 152 at the center turn point 305E.

In the series of FIGS. 4A-4E, it can be observed that the center turn point 305 moves from infinity (FIG. 4A) to near the PSC 152 at point 305E as the wheels are turned toward the left away from center. The center turn point would similarly move from infinity to near the PSC 152 as the steerable wheels 205L,205R are turned toward the right away from center.

Referring momentarily to FIG. 8, the steering linkage and steerable wheels are positioned to execute a left turn. The steerable wheels 205L,205R are pointed to the right so that the axes 301, 302G, 303G substantially intersect at the left center turn point 305G.

In the series of FIGS. 4A-4E and 8, the steerable wheels 205L,205R are pointed in the same direction. However, in one embodiment of the invention, the steerable wheels 205L, 205R can be controlled by the tiller 202 so that they point in different directions.

Figure 5:
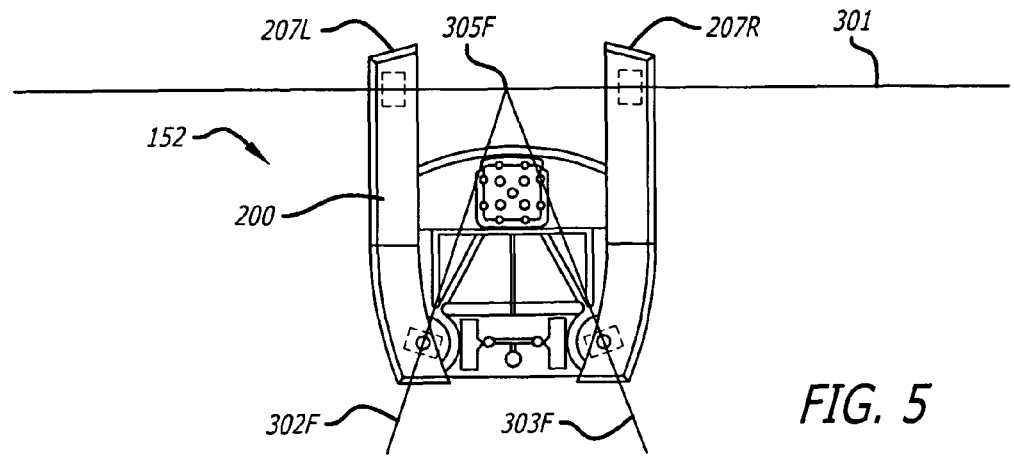
FIG. 5 is a diagram illustrating the desired steering linkage behavior for a zero radius turn of the mobile base and patient side cart.

In FIG. 5, the PSC 152 is executing a "Zero Radius" turn. The steerable wheels 205L,205R are pointed in different directions so that the axes 301, 302F, 303F substantially intersect within the PSC 152 at the center turn point 305F. The "zero radius turn" is a special case where the PSC 152 turns around a point 305F directly between the "pontoons" 207L, 207R of the mobile base 200. Depending upon which direction the tiller 202 is turned, the motor 212 for motorized wheel 205L is controlled in one direction while the motor 212 for the motorized wheel 205R is controlled to move in the opposite direction to execute the zero radius turn.

While a zero radius turn can be accomplished by the embodiments of the steering linkage disclosed herein, it has been mechanically prevented in a number of embodiments of the invention to avoid the complex motor control required to drive the motorized wheel 205L in one direction while driving the motorized wheel 205R in the opposite direction. Instead, the smallest radius turn has been limited to have a radius of approximately equal to half the width of the PSC 152.

The use of the four wheels 204L,204R,205L,205R greatly increases the stability of the PSC 152 over that of tri-pod wheel systems while maintaining the maneuverability and the intuitive steering found in three-wheel designs.

While a mechanical steering linkage may be used to steer the mobile base 200, the steering may also be electronically controlled in an alternate embodiment of the invention. In this case, the tiller may generate an electronic signal representing a tiller angle that is processed to generate a left wheel angle and a right wheel angle that is respectively transferred to a left electrical motor and a right electrical motor to respectively turn a left steerable wheel and a right steerable wheel directly or through a drive train or mechanical linkage.

Steering Mechanism

For a particular cart configuration (wheelbase, distance between front wheels, distance between back wheels, etc) the left and right steering angles can be computed which provide the "ideal Ackerman" steering system geometry.

Figure 6:
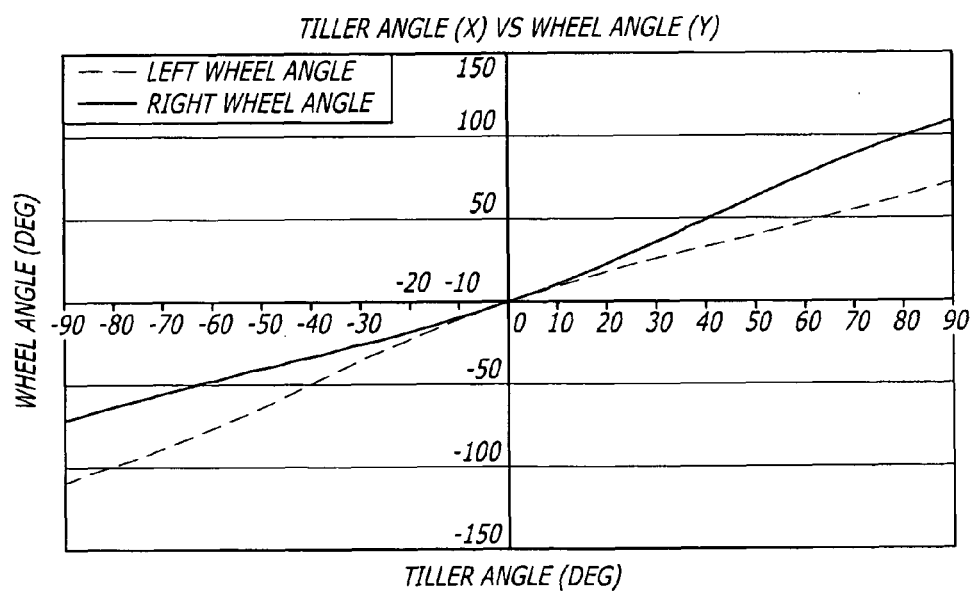
FIG. 6 is a graph of the tiller angle TA versus the left wheel angle LWA and the right wheel angle RWA of the steerable wheels of the mobile base.

FIG. 6 illustrates a graph showing the tiller angle TA (steering input) versus the left wheel angles (LWA) and the right wheel angles (RWA) to provide the proper steering behavior for an exemplary mobile base 200 having a wheelbase of thirty-four inches and a front and rear wheel separation (track width) of twenty-three inches in one embodiment of the invention.

When the tiller is positioned at center having a tiller angle (TA) of zero degrees, as is illustrated in FIG. 4A, a left wheel angle (LWA) of the left steerable wheel 205L and a right wheel angle (RWA) of the right steerable wheel 205R are also substantially zero degrees. However, when the tiller is moved away from center so that the TA is not zero degrees, the right wheel angle and the left wheel angle change from zero but at different rates. That is, for a given TA greater than or less than zero, the RWA and the LWA are not equal.

In one embodiment of the invention, the tiller 202 moves over the range of tiller angles from positive ninety degrees to negative ninety degrees. In another embodiment of the invention, the tiller 202 moves over the range of tiller angles from positive seventy degrees to negative seventy degrees.

Figure 7:
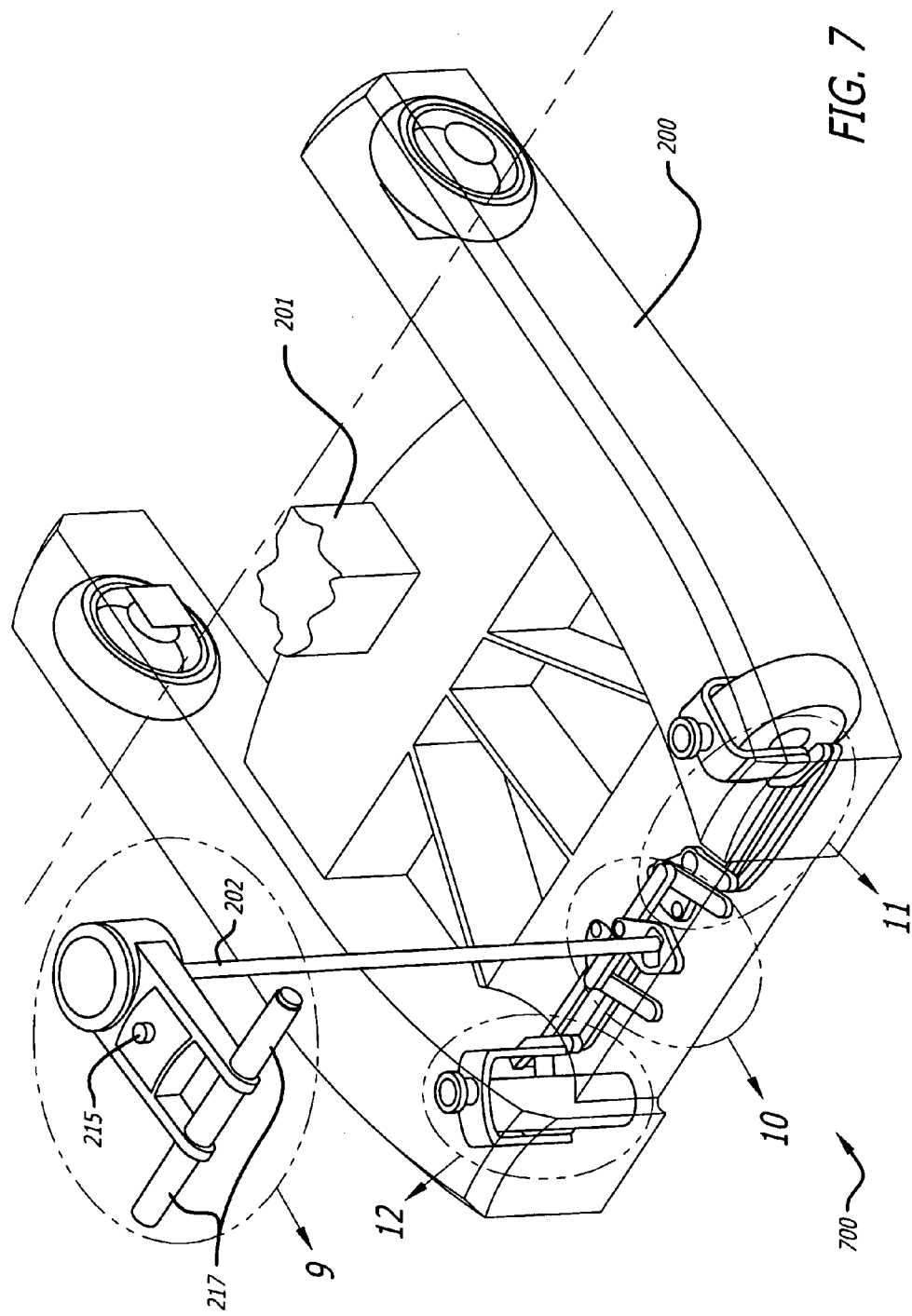
FIG. 7 is a perspective cutaway view of the mobile base to illustrate the steering system of the patient side cart.

Referring now to FIG. 7, a perspective cutaway view of the mobile base 200 is illustrated. The steering system 700 of the mobile base 200 and PSC 152 consists of four major subassemblies.

The first subassembly of the steering system 700 of the mobile base 200 is a steering tiller subassembly 900. The steering tiller subassembly 900 includes the tiller 202 with handlebars which an equipment operator EO uses to steer the PSC. The steering tiller subassembly 900 receives the input steering angle (also referred to as the tiller angle TA) from the operator EO. The steering tiller subassembly 900 is better illustrated in FIG. 9.

The second subassembly of the steering system 700 of the mobile base 200 is a steering function generator 1000. The steering function generator 1000 is a slot/cam/parallelogram mechanism which generates the proper wheel angles (LWA and RWA) as a function of the input steering angle (also referred to as the tiller angle TA). The steering function generator 1000 is better illustrated by FIG. 10.

The third subassembly of the steering system 700 of the mobile base 200 is a pair of -four-bar, Sine/Cosine parallelogram linkages 1100L, 1100R. Each side of the four-bar, Sine/Cosine parallelogram linkages transfers the "wheel angles" from the cam mechanism to the left and right wheel assemblies 1200L, 1200R. The right side four-bar, Sine/Cosine parallelogram linkage 1100R is better illustrated by FIG. 11. With a centered tiller at a tiller angle (TA) of zero degrees the assembly of the components of the steering system is symmetric about a centerline of the PSC 152 such that the left side four-bar, Sine/Cosine parallelogram linkage is a mirror image of the right side.

The fourth subassembly of the steering system 700 of the mobile base 200 is the pair of steerable wheel assemblies 1200L,1200R. The positions of the steerable wheels in the steerable wheel assemblies 1200L, 1200R control the direction of the mobile base around flooring. A steerable wheel assembly 1200 for each of the pair of steerable wheel assemblies 1200L, 1200R is better illustrated by FIG. 12.

Referring now to FIG. 8, a top cutaway view of the mobile base 200 is illustrated without the steering tiller subassembly. FIG. 8 illustrates the steering function generator 1000 coupled to the left and right four-bar, Sine/Cosine Parallelogram linkage 1100L, 1100R. FIG. 8 further illustrates the left and right four-bar, Sine/Cosine Parallelogram linkage 1100L, 1100R coupled to respective left and right steerable wheel assemblies 1200L,1200R.

FIG. 8 also illustrates a top view of the left and right motorized wheel assemblies 1200L, 1200R including the motorized wheels 204L,204R. Each assembly includes a sprocket 804 to couple to the drive train 214 that is driven by the motor 212 (see FIG. 2B). The sprocket 804 is further coupled to a rim of the motorized wheel to drive the wheel. A chain, belt, and/or one or more additional gears in the drive train 214 couples the sprocket 804 to the electric motor 212. Each assembly further includes a first bearing 807 and a second bearing 806 rotatably coupling a shaft of motorized wheel 204L,204R to the chassis 210 of the mobile base 200.

Figure 9:
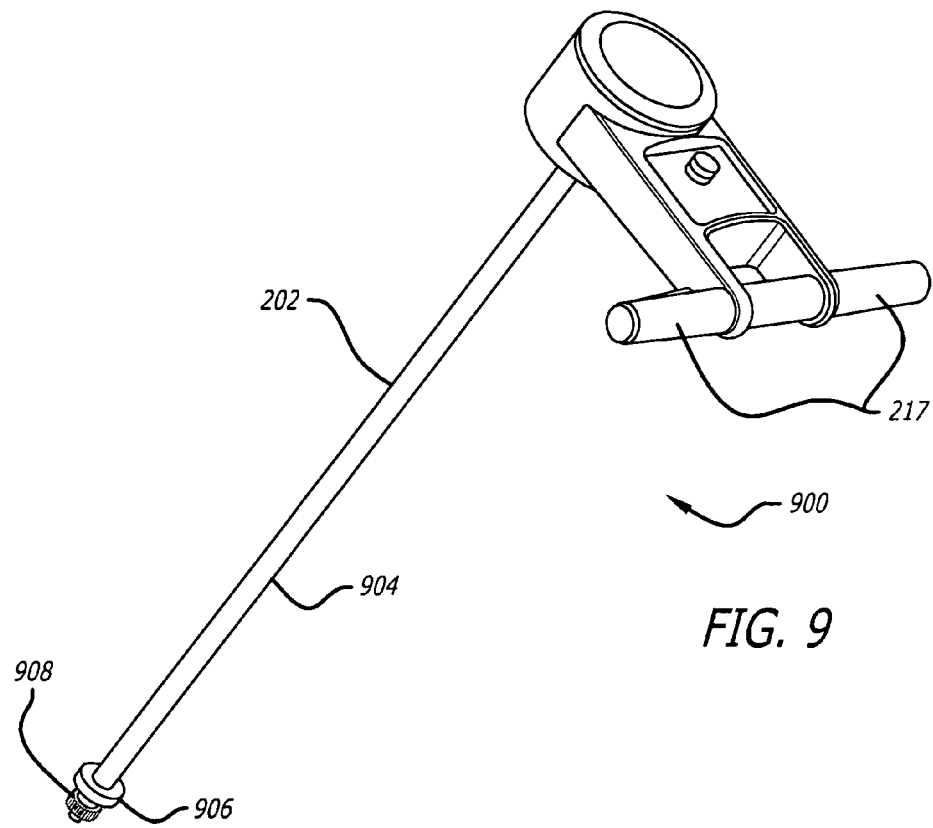
FIG. 9 illustrates a perspective side view of a steering tiller subassembly removed from the mobile base.

Referring now to FIG. 9, a perspective side view of the steering tiller subassembly 900 removed from the mobile base 200 is illustrated. As discussed previously, the steering tiller subassembly 900 receives the input steering angle (also referred to as the tiller angle TA) from an equipment operator EO that turns the tiller 202.

The steering tiller subassembly 900 includes the tiller 202 having a tiller shaft 904 and handlebars 217 coupled to the shaft at one end as illustrate in FIG. 9. An equipment operator EO uses the handlebars to rotate the shaft 904 to steer the PSC 152. The steering tiller subassembly 900 further includes a pinion gear 908 coupled to the shaft 904 of the tiller 202 near an end opposite the handlebars 217. The steering tiller subassembly 900 further includes a pair of spaced apart bearings 906 which are coupled to the shaft 904 between the gear 908 and the handlebars 217. The pair of bearings 906 rotatably couple the tiller 202 to the chassis 210 of the mobile base 200.

Figure 10:
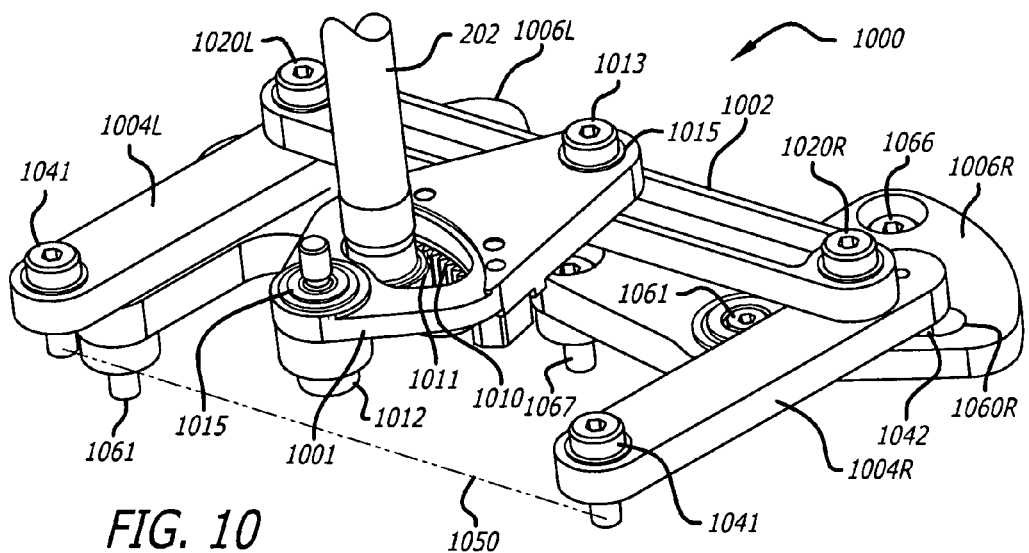
FIG. 10 illustrates a perspective side view of a function generator subassembly removed from the mobile base.

Referring now to FIG. 10, a perspective side view of the function generator subassembly 1000 removed from the mobile base 200 is illustrated. As discussed previously, the steering function generator 1000 generates the proper wheel angles (LWA and RWA) as a function of the input steering angle (also referred to as the tiller angle TA) received from the steering tiller subassembly 900.

The steering function generator 1000 is a slot/cam/parallelogram mechanism including a tiller link 1001; a long link 1002 (may also referred to as a sliding bar); left and right short links 1004L,1004R (may also referred to as ground links); and left and right cam plates 1006L,1006R with each having an angled arm and a cam follower slot. The two short links 1004-1004R, the tiller link 1001, and the long link 1002, along with ground of the chassis 210, form a parallelogram structure 1050.

The tiller link 1001 is pivotally coupled to the chassis 210 of the mobile cart 200 near one end by a pivotal shaft 1012. Near an opposite end, the tiller link 1001 is pivotally coupled to the long link 1002 by a pivotal shaft 1013. The pivotal shaft 1012 is coupled to the chassis 210. The pivotal shaft 1013 is coupled to the long link 1002. Bearings 1015 in the tiller link 1001 around the pivotal shafts 1012-1013 allow the tiller link 1001 to pivot about each.

The tiller link 1001 includes an opening or slot 1011 through which the tiller 202 and pinion gear 908 are inserted. An internal sector gear 1010, an arctuate gear segment, is rigidly coupled to the tiller link 1001 by bolts (not shown in FIG. 10). The internal sector gear 1010 meshes with the pinion gear 908 of the tiller 202 to receive the rotation of the tiller 202. In this manner, the tiller link 1001 and steering function generator 1000 receive the rotation of the tiller 202 that represents the tiller angle TA. Note that the tiller 202 may couple to the tiller link 1001 in other ways such as through a belt and pulley system, a chain and gear system, or a direct-drive.

The angular rotation of the tiller 202 causes the tiller link 1001 to pivot at one end about the pivotal shaft 1012 coupled to the chassis 210. The pivotal movement in the tiller link 1001 is linearly coupled to the long link 1002 through the pivotal shaft 1013. That is, the tiller link 1001 substantially converts the angular rotation of the tiller 202 into a lateral sweeping motion of the long link 1001.

The long link 1002 pivotally couples to the left short link 1004L through a pivotal shaft 1020L near one end and to the right short link 1004R through a pivotal shaft 1020R near an opposite end. The pivotal shaft 1020L is coupled to the left short link 1004L. The pivotal shaft 1020R is coupled to the right short link 1004R. Bearings in the long link 1002 around the pivotal shafts 1020L-1020R allow the long link 1002 and the short links 1004L-1004R to pivot respectively about each other there-at. In one embodiment of the invention, the bearings around the pivotal shafts are needle bearings but could also be roller bearings or other types of ball bearings.

The long link 1002 converts its lateral sweeping motion (may also referred to as a linear sweeping motion) into pivotal motion of each of the short links 1004L-1005R. In essence, the pivotal motion of the tiller link 1001 is coupled into pivotal motion in each of the short links 1004L, 1004R by the long link 1002.

As illustrated in FIG. 10, the left and right short links 1004L,1004R each include a cam follower 1042 (see also FIG. 14) near a first end that is inserted into cam follower slots 1060L,1060R in each of the left and right cam plates 1006L,

1006R, respectively. Also near the first end of each of the short links 1004L,1004R, the short links 1004L,1004R are pivotally coupled by pivotal shafts 1020L,1020R to the long link 1002 near its opposite ends. The pivotal shafts 1020L, 1020R are coupled to the short links 1004L,1004R, respectively. Near the second end of the left and right short links 1004L, 1004R opposite the first end, each of the left and right short links 1004L,1004R are pivotally coupled to the chassis 210 by pivotal shafts 1041. The pivotal shafts 1041 are coupled to the chassis 210. Bearings in the left and right short links 1004L, 1004R around the pivotal shafts 1041 allow the short links to pivot at the axis of the pivotal shafts 1041. Bearings in the long link 1001 around the pivotal shafts 1020L, 1020R allow the short links to pivot at the axis of the pivotal shafts 1020L,1020R.

As discussed previously, a cam follower 1042 of each short link 1004L,1004R is inserted into cam follower slots 1060L, 1006R in each respectively cam plate 1006L, 1006R. The pivotal motion of the short links 1004L,1004R is converted into a rotational or pivotal motion of varying degrees in the cam plates 1006L,1006R about pivotal shafts 1061 by the cam follower and cam follower slots. In one embodiment of the invention, the cam follower slots 1060L, 1060R are linear in shape to provide a linear cam profile. In other embodiments of the invention, the cam follower slots may be curved to provide a curved cam profile or have a complex shape to provide a complex cam profile. Note that the cam slots should be slightly wider than the maximum diameter of the cam follower. That is, the diameter of the cam followers 1042 should be less than the width of the cam follower slots 1060L, 1060R so that there may be a small gap to one side. This is to prevent "scrubbing" (rubbing on both sides simultaneously) of the cam followers in the cam follower slots. The larger width of the cam slots over the diameter of the cam follower slots contributes a small amount of backlash, but reduces wear and friction in the steering system.

As shown in FIGS. 10, 11, 13, and 15, the cam plates 1006L,1006R have a pair of angled arms forming a letter-V-like shape that pivot about the pivotal shafts 1061 near a base. As shown in FIGS. 10, 11, 13, and 15, a cam follower slot 1060L,1060R,1060 is formed along a portion of the angled arm of each cam plate 1006L,1006R,1006. The cam plates 1006L,1006R are mirror images of each other. However, the cam plates 1006L,1006R are pivotally mounted with their angled arms forming the letter-V-like shapes pointing outward towards the respective left and right wheel assemblies with their pivot points oriented toward the center of the cart. The cam plates 1006L,1006R provide varying and different degrees of wheel angle (LWA,RWA) in the left and right steerable wheels, such as illustrated in FIG. 6.

Figure 11:
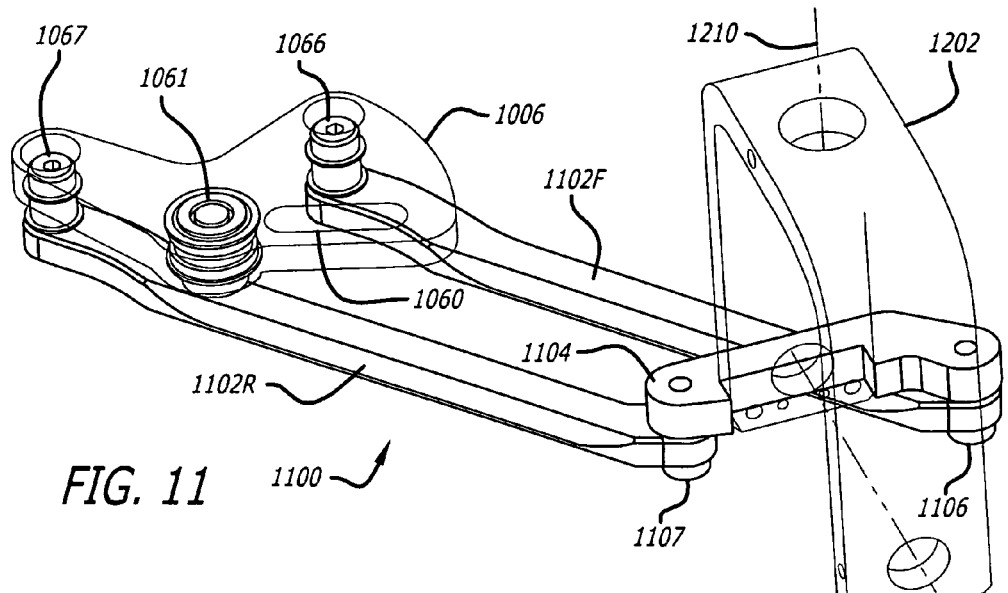
FIG. 11 illustrates a perspective side view of parallelogram linkage removed from the mobile base.

Inserted in each of the cam plates 1006L,1006R are bearings around the pivotal shafts 1061 to allow them to pivot around the axis there-at. The pivotal shafts 1061 are coupled to a pair of pivot plates (see pivot plates 1606L,1606L in FIG. 16) that are coupled to the chassis 210. In this manner, the cam plates 1006L, 1006R are pivotally coupled to the chassis 210. Near the tops of the letter-V-like shape, each angled arm of the cam plates 1006L, 1006R pivotally couple to a pair of steering links (that may also referred to as tie rods) of the parallelogram linkage 1100L,1100R through the pivotal shafts 1066-1067 (see FIG. 11). As shown in FIG. 11, the respective cam plates 1006 are coupled to the respective left and right wheel assemblies through the parallelogram linkage 1100 to steer the steerable wheels.

Referring now to FIG. 11, a perspective side view of one parallelogram linkage 1100 removed from the mobile base 200 is illustrated. The parallelogram linkage 1100 that is illustrated in FIG. 11 is the right side parallelogram linkage 1100R. When the tiller is centered with a tiller angle of zero degrees the steering system is symmetric about a center line such that the left side parallelogram linkage 1100L is a mirror image of the right side parallelogram linkage 1100R having substantially similar components.

The parallelogram linkage 1100 includes the cam plate 1006, a rear steering link 1102R, a front steering link 1102F, and a caster link 1104 pivotally coupled together at the pivotal shafts 1066,1067,1106,1107 as illustrated in FIG. 11. Through the pivotal shafts 1067 and 1107, the ends of the rear steering link 1102R are pivotally coupled to the cam plate 1006 and the caster link 1104 near a first end of each. Through the pivotal shafts 1066 and 1106, the ends of the front steering link 1102F are pivotally coupled to the cam plate 1006 and the caster link 1104 near a second end of each opposite their first ends.

The caster link 1104 is coupled to a caster bracket 1202 to steer one of the steerable wheels.

Figure 12:
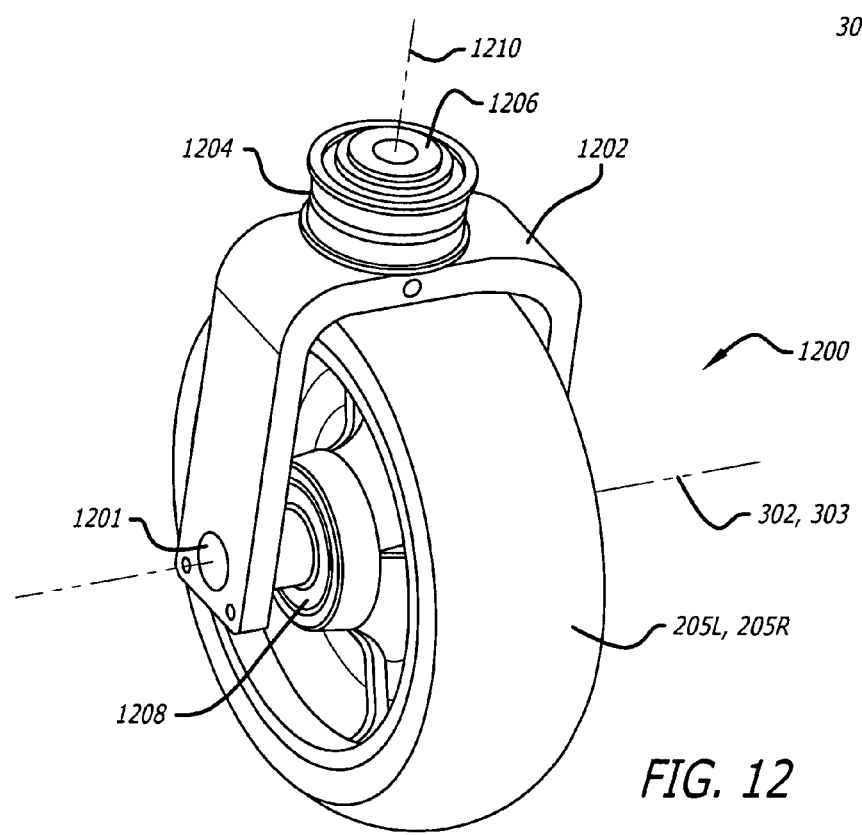
FIG. 12 illustrates a perspective side view of a wheel assembly removed from the mobile base.

Referring momentarily to FIG. 12, each caster bracket 1202 of each wheel assembly 1200 is pivotally coupled to the chassis 210 by one or more bearings 1204 through the pivotal shaft 1206. The pivotal shaft 1206 is rigidly coupled to the caster bracket 1202 so that they pivot together as a pivoting assembly. The caster bracket 1202 and the wheel assembly 1200 pivot about the axis 1210 through the pivotal shaft 1206 as illustrated in FIGS. 11 and 12.

Referring now back to FIG. 11, the rotational motion of the cam plate 1006 is converted into equal but opposite lateral sweeping motion in the rear steering link 1102R and the front steering link 1102F. As the rear steering link 1102R is pushed laterally by the cam plate 1006, the front steering link 1102F is laterally pulled on by the cam plate. Accordingly, the rear steering link 1102R pushes on the first end of the caster link 1104 and the front steering link 1102F pulls on the second end of the caster link 1104. In response, the caster link 1104 pivots in one direction around the axis 1210. Conversely, as the front steering link 1102F is laterally pushed by the cam plate, the rear steering link 1102R is laterally pulled on by the cam plate. Accordingly, the rear steering link 1102R pulls on the first end of the caster link 1104 and the front steering link 1102F pushes on the second end of the caster link 1104. In response, the caster link 1104 pivots in an opposite direction around the axis 1210. In this manner, the rotational or pivotal motion of the cam plate 1006 is transferred out to the caster link 1104 by the parallelogram linkage 1100.

Between the left parallelogram linkage 1100L and the right parallelogram linkage 1100R, the distance of lateral movement in the rear steering link 1102R and the front steering link 11102F differs so that the LWA and the RWA differ, such as illustrated in FIG. 6 for example.

Referring now to FIG. 12, a perspective side view of the wheel assembly 1200 removed from the mobile base 200 is illustrated. The wheel assembly 1200 includes the steerable wheel 205L,205R, an axle 1201, bearings 1208, the caster bracket 1202, bearings 1204, and pivotal shaft 1206. The steerable wheel 205L,205R is rotatably coupled to the caster bracket 1202 by the axle 1201 and the bearings 1204. The axle 1201 of the steerable wheel 205L,205R is substantially concentric to the axis 302,303. Thus, each steerable wheel 205L, 205R rotates about its axle 1201 and its respective axis 302, 303.

As discussed previously, the caster link 1104 is coupled to the caster bracket 1202 to steer the steerable wheel 205L, 205R. Thus, the pivotal motion of the caster link 1104 is coupled to the caster bracket 202 and the steerable wheel 205L,205R. The caster link 1104, the caster bracket 1202, and the wheel assembly 1200 pivot about the axis 1210 through the pivotal shaft 1206 in response to the linear movement in the rear steering link 1102R and the front steering link 1102F. That is, the pivotal motion of the cam plate 1006L,1006R is couple into pivotal motion of the wheel assembly 1200 through the parallelogram linkage 1100. Note that another wheel may be included in the wheel assembly 1200 to form a double wheeled assembly for greater load carrying capability.

The wheel contact patch of each steerable wheel 205L, 205R does not have to be located directly below the axis 1210 of rotation of the wheel assembly 1200. In this case, the wheel contact patch is slightly offset (such as approximately three-fourths of an inch for example) from the axis 302,303 of rotation of the center of the wheel. The wheel should to be sufficiently offset so that the actual contact patch of the tire/wheel is offset to one side of the center axis 302,303 of rotation.

The offset in the wheel contact patch keeps the wheel from "scrubbing" on the floor (marking, wear) and instead enables the wheel to roll around the axis of rotation with less resistance to the equipment operator EO moving the tiller. Otherwise, if the wheels were centered so that the contact patch was in line with the axis 1201 over the center axis 302,303, the scrubbing of the on-axis contact patch can generate high resistance that is felt by the operator EO. Various amounts of scrubbing can occur if the center of rotation 302,303 is inside of the contact patch with the flooring.

Operation

Figure 13:
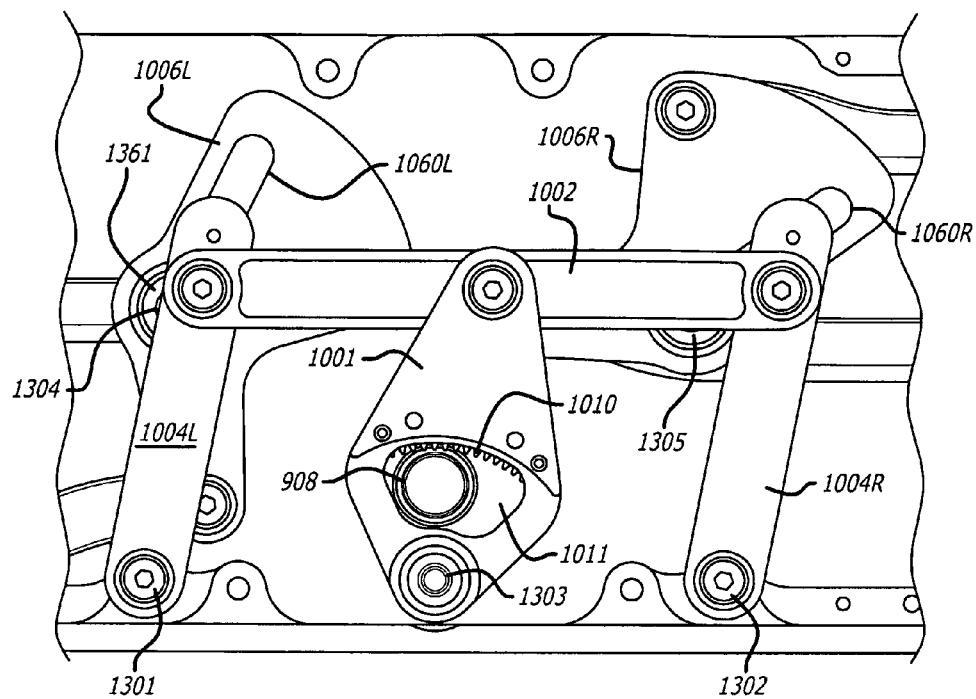
FIG. 13 illustrates a top view of a portion of the steering system mounted in the mobile base of the patient side cart.

Reference is now made to FIG. 13 illustrating a top view of a portion of the function generator 1000. FIG. 13 better illustrates the cam plate 1006L,1006R and their respective cam follower slots 1060L,1060R. FIG. 13 illustrates the pivot bearing 1361 in the cam plate 1006L to pivot the cam plate about the pivotal shaft 1061.

In operation, an equipment operator EO holds the tiller handles 217 to turn the tiller 202 and steer the PSC 152. The tiller 202 rotates approximately ±70° from the straight-ahead or centered position. The tiller handles 217 turn the tiller shaft 904 and the pinion gear 908 coupled near its end. In one embodiment of the invention, the pinion gear 908 has twenty-three teeth. The pinion gear 908 meshes with an internal sector gear 1010, an arctuate gear segment. If the internal sector gear 1010 were completely fully circular, it would have eighty teeth in one embodiment of the invention. Thus, the gear ratio between the internal sector gear 1010 and the pinion gear 908 is eighty over twenty-three or 3.478 to 1.

The internal sector gear 1010 is attached to the tiller link 1001. The tiller shaft 904 passes through a slot 1011 in the tiller link 1001. The slot 1011 restricts the angular motion of the tiller link 1001 to plus and minus twenty degrees around the pivot axis 1303. In FIG. 13, the tiller link 1001 is shown at approximately eleven degrees clockwise from its centered position.

As discuss previously, the two short links 1004L,1004R, the tiller link 1001, and the long link 1002, in addition to ground, form a pivotable parallelogram structure 1050. Pivot axes 1301, 1302, and 1303 of the pivotable parallelogram structure are grounded. As the tiller link 1001 is driven back and forth by the tiller shaft pinion gear 908, the two short links 1004L, 1004R move in a substantially similar way.

Note that pivotable parallelogram mechanism 1050 is technically over constrained due to the presence of three parallel links—the two short links 1004L, 1004R and the tiller link 1001. However in practice, the manufacturing precision of the components is very good and the inherent compliance of the assembled mechanism allows the pivotable parallelogram mechanism 1050 to function well without binding. Note that the ground pivot of the tiller link 1001 at axis 1303 is allowed to float on a separate mounting plate during assembly and thus can find the optimal assembly location before being tightened down.

Figure 14:
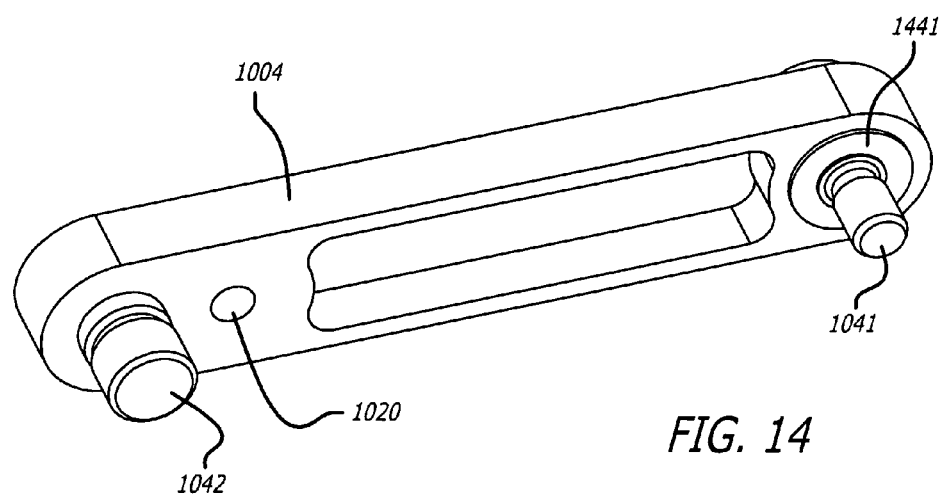
FIG. 14 illustrates a side perspective view of a short link for the steering system of the mobile base and patient side cart.

Referring now to FIG. 14, a bottom perspective view of a short link 1004 is illustrated. FIG. 14 better illustrates the cam follower 1042 attached near the end of each of the two short links 1004L,1004R. Each cam follower 1042 engages the cam follower slot 1060L,1060R machined into the respective cam plates 1006L, 1006R. FIG. 14 better illustrates the bearing 1441 inserted in the short link 1004 so the link can pivot about the pivotal shaft 1041. FIG. 14 also illustrates a back side of a pivotal shaft 1020 coupled to the short link 1004 where the long link 1002 may be pivotally coupled.

Figure 15:
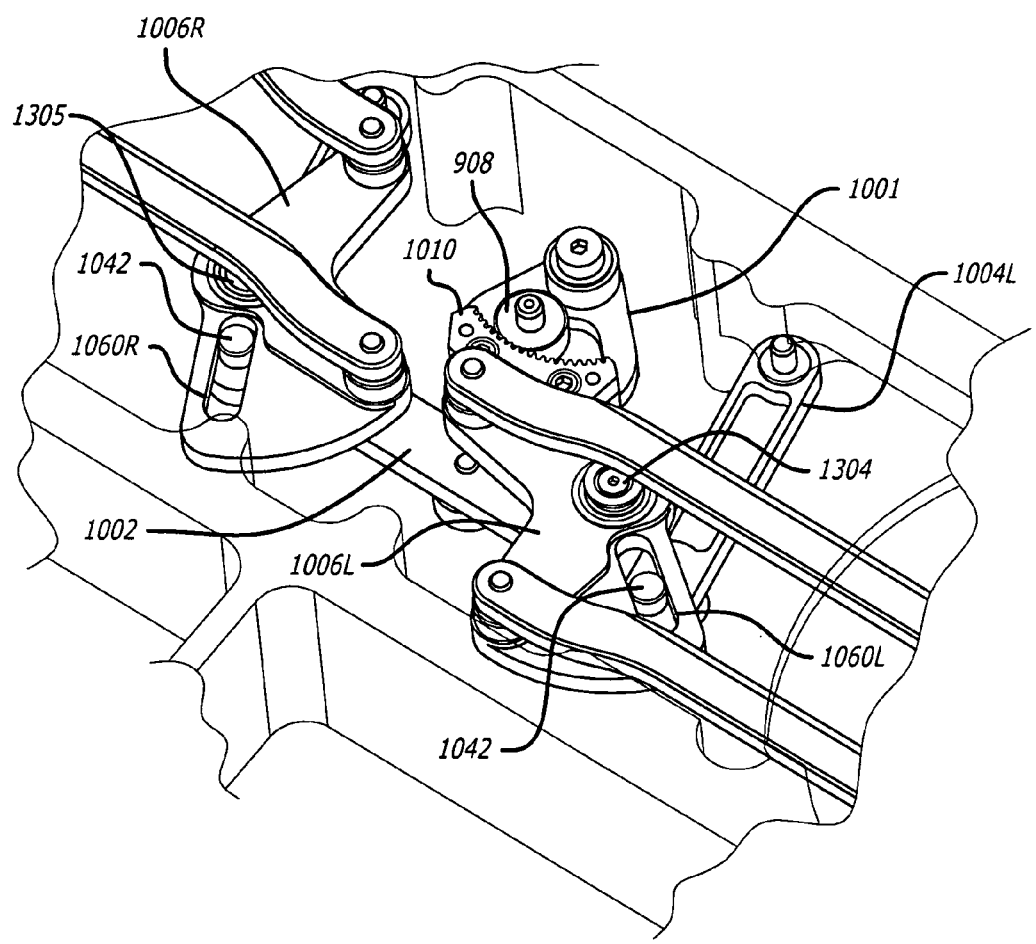
FIG. 15 illustrates a bottom side perspective view of a portion of the steering system mounted in the mobile base of the patient side cart.

Referring now to FIG. 15, a bottom cutaway perspective view of a portion of the steering mechanism of the PSC 152 is illustrated. FIG. 15 better illustrates the cam followers 1042 of each short link 1004L,1004R respectively within the cam follower slots 1060L,1060R of the cam plates 1006L,1006R. FIG. 15 further illustrates the meshing of the pinion gear 908 of the tiller 202 with the gear sector 1010 of the tiller link 1001.

As the pivotable parallelogram mechanism 1050 moves back and forth driven by the tiller 202, the cam followers 1042 drive the left cam plate 1006L and the right cam plate 1006R in a unique way. Through the combination of link lengths, pivot locations, and geometric relationships, the motion of the cam plates 1006L,1006R creates the left and right angular motions required to substantially generate Ackerman motion to the steerable wheels 205L, 105R over the complete range of turning radii, from infinite radius (straight running) to zero radius (pivoting about a point between the front wheels) in either left or right turn directions.

Referring now back to FIG. 13, the left cam plate 1006L pivots about the grounded axes 1304 and the right cam plate 1006R pivots about the grounded axis 1305. The left short link 1004L pivots about the grounded axis 1301 and the right short link 1004R pivots about the grounded axis 1302.

Figure 16:
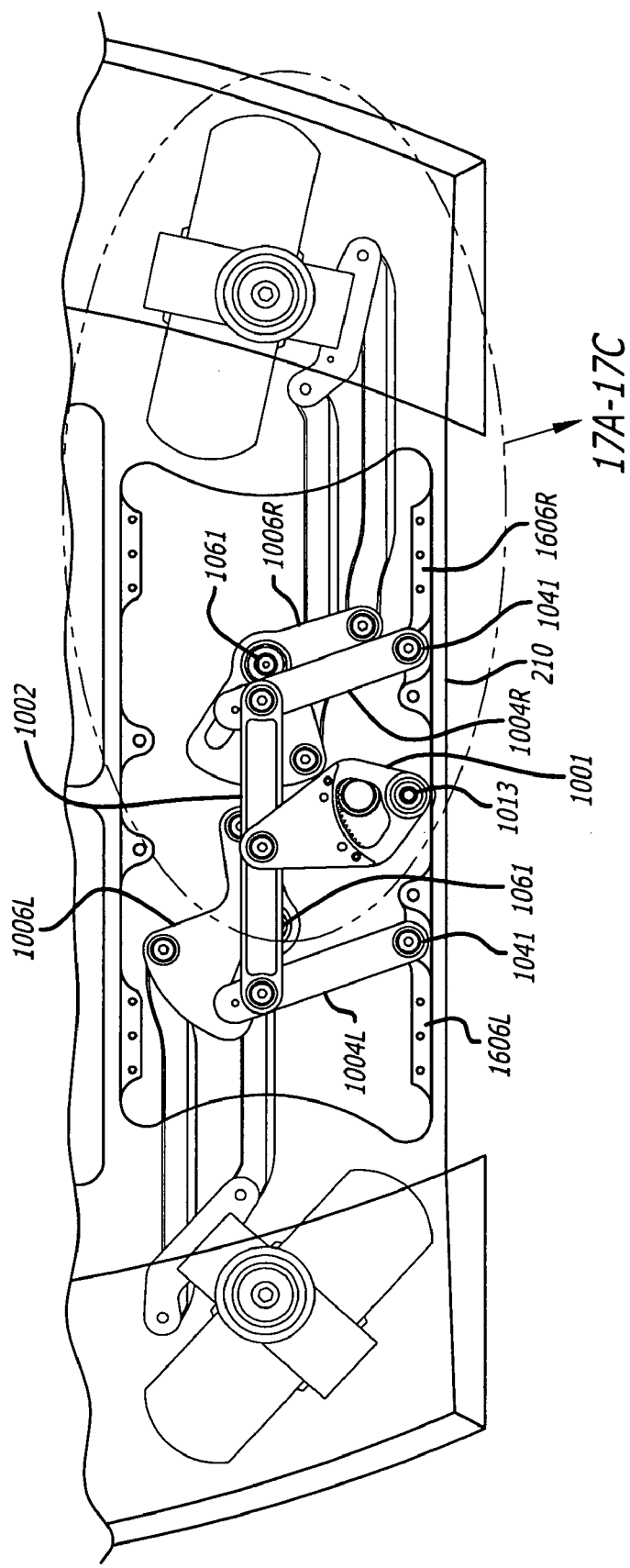
FIG. 16 illustrates a top view of the steering system mounted in the mobile base of the patient side cart.
Figure 17A:
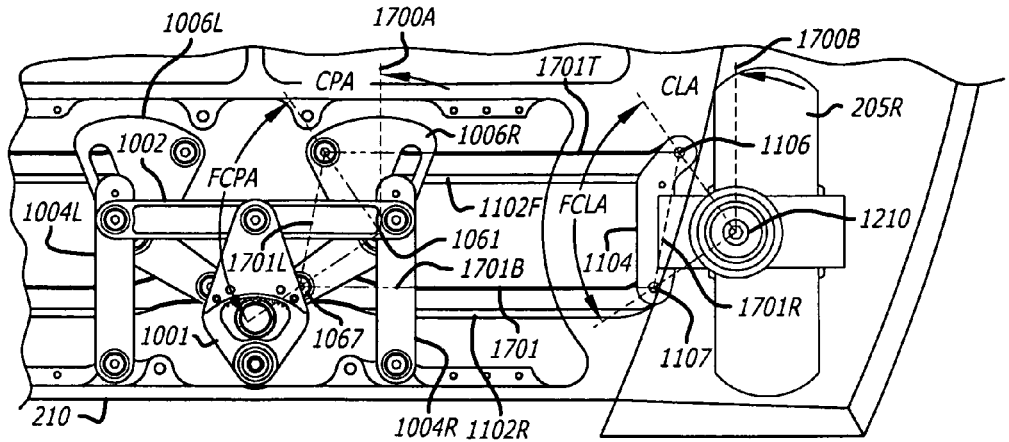
FIGS. 17A-17C illustrate the movement of the steering system and its linkage as it moves to steer left and right from center.
Figure 17B:
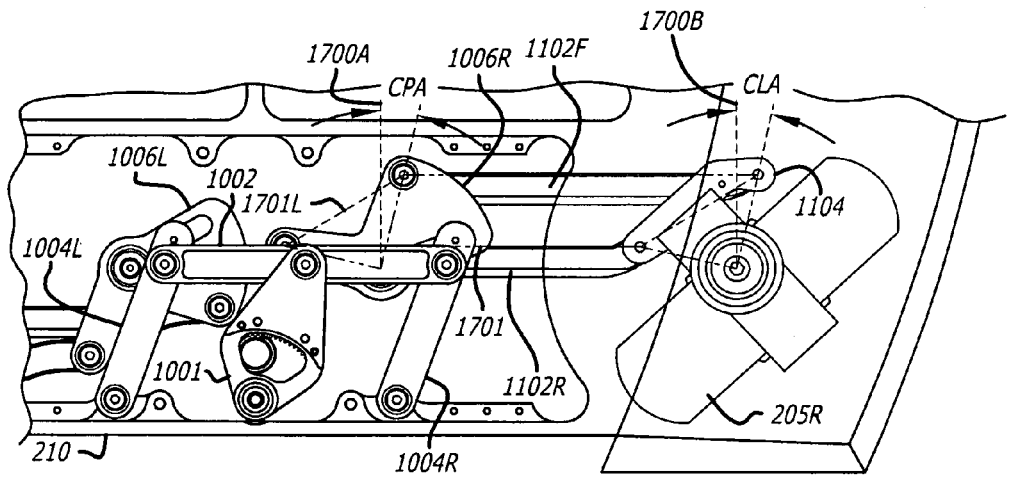
Figure 17C:
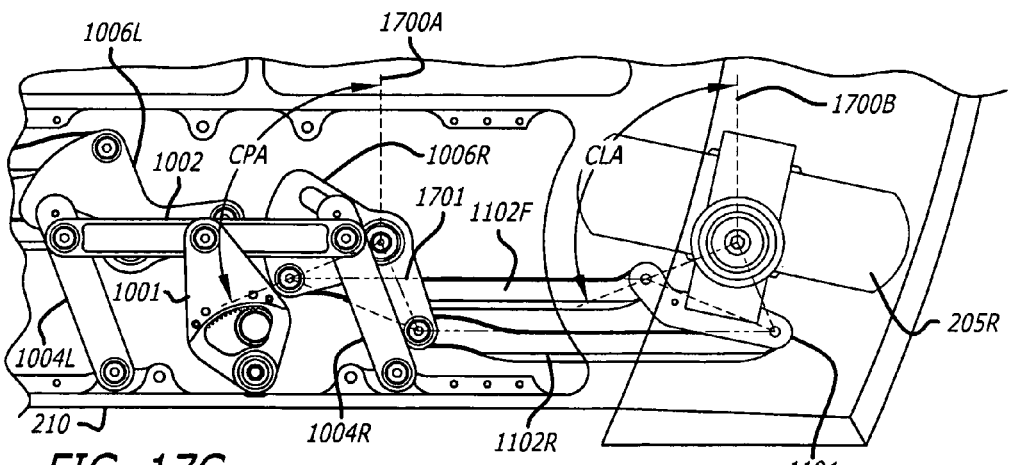

Reference is now made to FIGS. 16 and 17A-17C. FIG. 16 illustrates both left and right sides of the steering system and its linkage. FIGS. 17A-17C illustrate the right side of the steering system and the how the cam follower and the steering linkage move as the tiller is turned between right and left through center.

In FIG. 16, the pivot plates 1606L,1606R are illustrated coupled to the chassis 210. The pivotal shafts 1061, about which the cam plates 1006L,1006R pivot, are coupled to the pivot plates 1606L,1606R. FIG. 16 further illustrates how the short links 1004L,1004R are pivotally coupled to the chassis (ground) 210 at the pivotal shafts 1041 and how the tiller link 1001 is pivotally coupled to the chassis (ground) 210 at the pivotal shaft 1013.

As discussed previously with reference to FIG. 11, the right side parallelogram linkage 1100R includes the cam plate 1006R, a rear steering link 1102R, a front steering link 1102F, and a caster link 1104 pivotally coupled together at the pivotal shafts 1066,1067,1106,1107. The pivotal shafts form axes that are referenced using the same reference number for convenience.

In FIG. 17A, the steering system including the parallelogram linkage is positioned as illustrated in a nominal, straight running direction. That is, the steering system is centered so that the steerable wheels are straight and the mobile base 200 and PSC 152 moves in a straight direction when driven by the motorized wheels forwards or backwards. Additionally, the tiller link 1001 is centered and pointing in a straight direction. The long link 1002 is parallel to the axes 302,303 through the axles in the steerable wheels. The left and right short links 1004L-1004R are centered and pointing in a straight direction such that cam plates 1006L,1006R are in a centered position.

In FIG. 17A with the right steerable wheel 205R point straight, it has a right wheel angle (RWA) of substantially zero degrees with reference to line 1700B.

The right side parallelogram linkage 1100R forms a parallelogram 1701 in FIGS. 17A-17C having a top side 1701T along the front steering link 1102F between axes 1066,1106, a bottom side 1701B along the rear steering link 1102R between axes 1067,1107, a left side 1701L along the cam plate 1006R between axes 1066,1067; and a right side 1701R along the caster link 1104 between axes 1106,1107 as illustrated in FIG. 17A. The left side parallelogram linkage 1100L forms a mirror image of the parallelogram 1701 when viewed with the tiller centered having a tiller angle of zero degrees. The parallelogram linkage 1100 maintains the parallelism between sides of the parallelogram 1701 as the parallelogram shifts and the angles between the sides 1701T,1701L,1701B,1701R of the parallelogram 1701 changes.

At the axis 1061 of the pivotal shaft 1061 about which the cam plate 1006R pivots, a fixed cam plate angle FCPA of ninety degrees is formed between lines out to each of the axis 1066 and 1067 along the arms or prongs of the letter-V-like shape of the cam plate. Similarly at the axis 1210 of the pivotal shaft 1206 of the wheel assembly 1200 (see FIG. 12), a fixed caster link angle FCLA of ninety degrees is formed between lines out to each of the axis 1106 and 1107 in the caster link 1104. For this reason, the parallelogram linkage may also be referred to as sine/cosine parallelogram linkage since the equations underlying the mechanical advantage computation of the linkage are sine and cosine waves that are offset by a FCPA and FCLA of ninety degrees. When one link's mechanical advantage is "going to zero", the other link's mechanical advantage is "going to maximum"—a property of sine and cosine waves While the fixed cam plate angle and the fixed caster link angle FCLA are ninety degrees in a preferred embodiment of the invention, other fixed angles between the arms of the cam plate and the arms of the caster link may be formed and diverge from an ideal Sine/Cosine parallelogram linkage.

A cam plate angle CPA and a caster link angle CLA can be defined in the steering linkage 1100R with reference to the lines 1700A-1700B in FIG. 17A-17C, respectively. The cam plate angle CPA is formed at the axis 1061 of the cam plate 1006R between a line extending between axis 1061,1066 and the line 1700A. The caster link angle CLA is formed at the axis 1210 of the wheel assembly 1200 between a line extending between axis 1210,1106 and the line 1700B. The CPA and the CLA are made to be equivalent angles by the steering linkage 1100R and the parallelogram 1701.

In FIG. 17A with the steering system centered, the CPA and CLA are approximately thirty-four degrees each in one embodiment of the invention.

In FIG. 17B, the steering system including the parallelogram linkage 1100 is positioned as illustrated to make a minimum radius left turn. Additionally, the tiller link 1001 is pivoted to the right. The long link 1002 is linearly shifted to the right from its centered position. The left and right short links 1004L-1004R are pivoted to the right from their centered positions such that cam plates 1006L,1006R are pivoted about their respective pivotal shafts 1061. The cam plate angle CPA and CLA are both approximately negative thirteen and one-half degrees in one embodiment of the invention.

In FIG. 17C, the steering system including the parallelogram linkage 1100 is positioned as illustrated to make a minimum radius right turn. Additionally, the tiller link 1001 is pivoted to the left. The long link 1002 is linearly shifted to the left from its centered position. The left and right short links 1004L-1004R are pivoted to the left from their centered positions such that cam plates 1006L,1006R are pivoted about their respective pivotal shafts 1061. The cam plate angle CPA and CLA are approximately positive one-hundred twelve and two-tenths degrees each in one embodiment of the invention.

Knowing the cam plate angle CPA with the vertical line 1700A (running from front to back on the PSC) and the caster link angle CLA with the vertical line 1700B are approximately negative 13.5 degrees for making a minimum left turn as illustrated in FIG. 17B and approximately 112.2 for making a right turn as illustrated in FIG. 17C, the right wheel angle RWA of the right steerable wheel 205R can be computed in each case.

Assuming the mobile base is moving forward and making a left turn with the linkage position as shown in FIG. 17B, the right steerable wheel 205R is the outer wheel along the turning radius. In one embodiment of the invention, the right steerable wheel 205R is moved to have a RWA of approximately negative forty-seven degrees (34 plus 13) with reference to line 1700B.

Assuming the mobile base is moving forward and making a minimum right turn with the linkage position as shown in FIG. 17B, the right steerable wheel 205R is the inner wheel along the turning radius and is to be turned more sharply. In one embodiment of the invention, the right steerable wheel 205R is moved to have a RWA of approximately positive seventy-eight degrees (112 minus 34) with reference to line 1700B in one embodiment of the invention.

Thus, in accordance with Ackerman steering principles, the PSC steering system and linkage turns the inner steerable wheel more sharply than the outer steerable wheel when making tight radius turns.

Figure 18A:
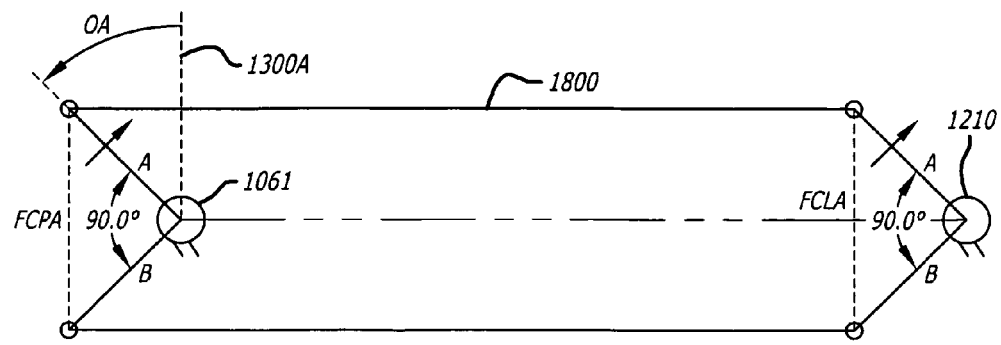
FIGS. 18A-18C illustrate schematic diagrams of the steering linkage in different positions.
Figure 18B:
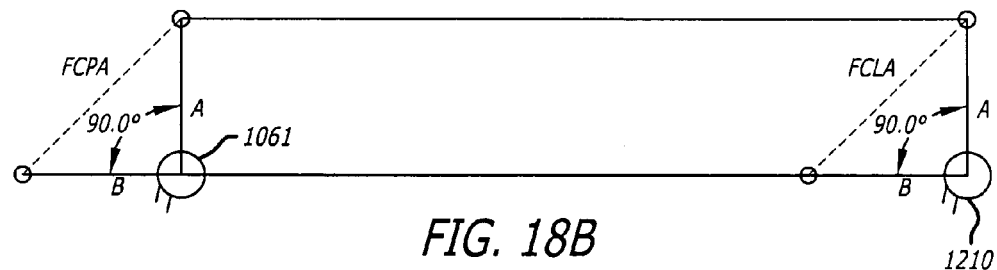
Figure 18C:
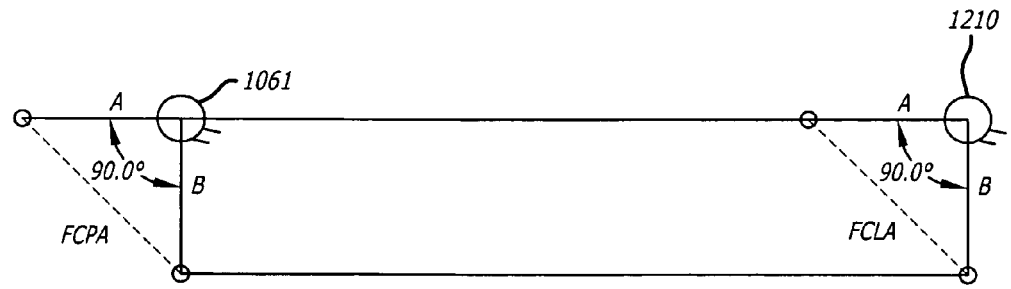

Reference is now made to FIGS. 18A-18C showing schematic illustrations of a parallelogram linkage 1800 and the application and transfer of torque. Additionally, a fixed cam plate angle FCPA of ninety degrees and a fixed caster link angle FCLA of ninety degrees are illustrated in FIGS. 18A-18C between arms A and B. While the fixed cam plate angle and the fixed caster link angle FCLA are ninety degrees in a preferred embodiment of the invention, other fixed angles between the arms of the cam plate and the arms of the caster link may be formed and diverge from an ideal Sine/Cosine parallelogram linkage.

In FIG. 18A, the parallelogram linkage 1800 is in a nominal position (e.g. arm A at forty-five degrees from vertical). Both of the arm pairs A-A and B-B are in a position to equally transmit torque from the pivotal shaft 1061 on the left to the pivotal shaft 1210 on the right (for example). The parallelogram linkage 1800 is coupled to chassis ground at the pivotal shafts 1061,1210.

In FIG. 18B, the parallelogram linkage 1800 has experienced a clockwise CW motion of forty-five degrees from the position illustrated in FIG. 18A. The arm pair A-A is positioned so that it has a maximum mechanical advantage, while the arm pair B-B is positioned so that all of its mechanical advantage is lost.

In FIG. 18C, the parallelogram linkage 1800 has experienced a counter-clockwise CCW motion of forty-five degrees from the position illustrated in FIG. 18A. The arm pair A-A is positioned so that it has lost all of its mechanical advantage, while the arm pair B-B is positioned so that it has a maximum mechanical advantage.

This illustrates that by using the parallelogram linkage disclosed herein that it is possible to transmit torque over a much larger range of motion than would be possible if only one arm pair (A-A or B-B) were used. For practical purposes, a single arm pair version might work well for ninety degrees or one-hundred degrees of motion. However, the parallelogram linkage disclosed herein with both arm pairs (A-A and B-B) can transmit torque effectively for a full rotation of three hundred sixty degrees. In one embodiment of the invention, torque is transferred over a range of motion of one-hundred twenty-five degrees. By maintaining a mechanical advantage over a range of motions in the parallelogram linkage, the steering of heavy mobile medical equipment can be eased by reducing the torque required to turn the tiller and the steerable wheels.

In FIG. 18A, there is an offset angle OA (previously referred to as cam plate angle CPA) between the longitudinal line 1300A and arm A on the left when the steering mechanism is centered. As this steering mechanism can transmit torque over a full rotation (360 degrees) which is not required for implementation, the initial offset angle is essentially a free variable and was chosen for reasons of mechanical packaging and mechanical clearance.

The parallelogram steering linkage has been shown to work very effectively for steering the PSC 152. The embodiments of the steering mechanism disclosed herein provides a small turning radius (theoretically down to a zero turning radius) (See FIG. 5). The embodiments of the invention provide a dual steering axis to increase stability and ease the steering of heavy mobile medical equipment, such as the PSC 152.

Alternate Steering Mechanism

FIGS. 7-17 illustrate a steering system between the steerable wheels 205L,205R that employs rotary joints and parallelogram linkage to provide a greater range of motion, a more compact size, and better aesthetics. Instead of parallelogram linkage, a linear sliding bar and a tiller cam arm may be employed.

Figure 19:
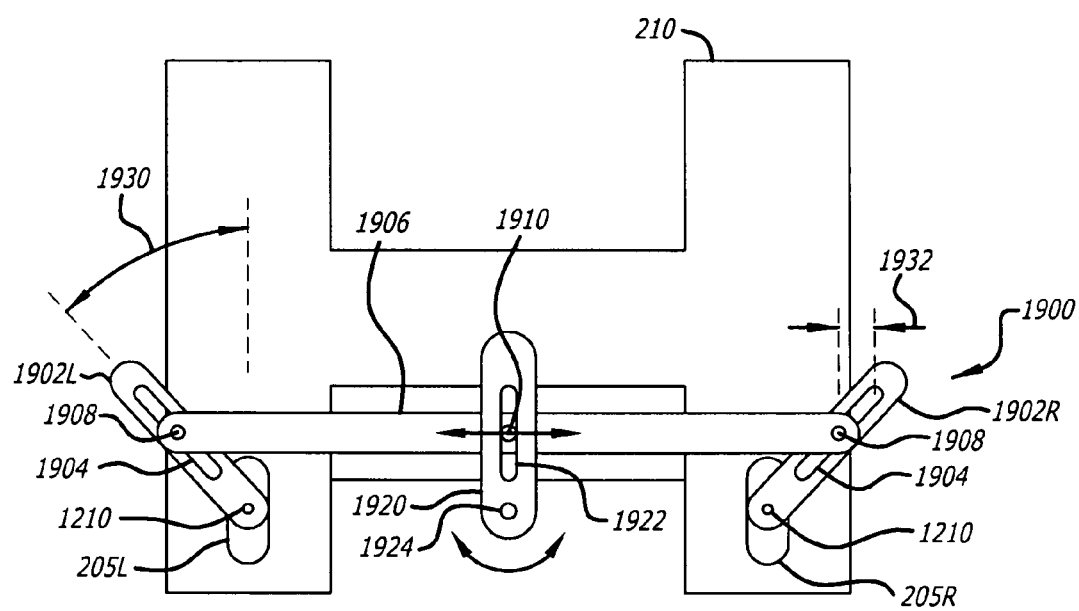
FIG. 19 illustrates a top view of another embodiment of a steering system for a patient side cart.
Figure 20A:
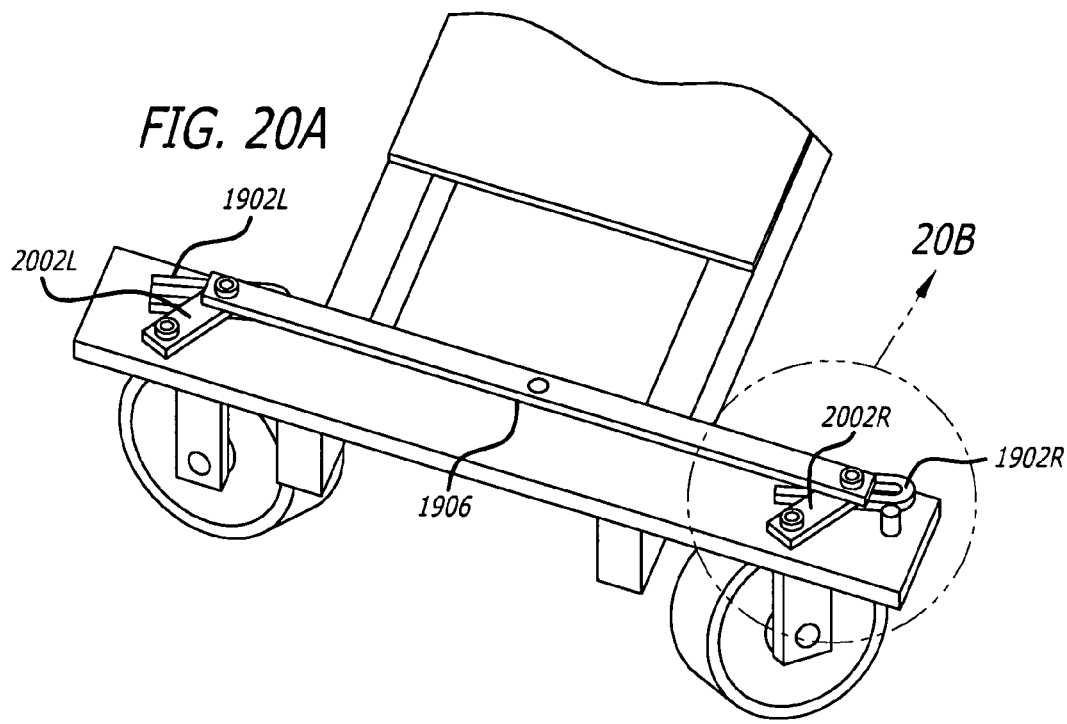
FIG. 20A illustrates a perspective view of the steering system of FIG. 19 for a patient side cart.
Figure 20B:
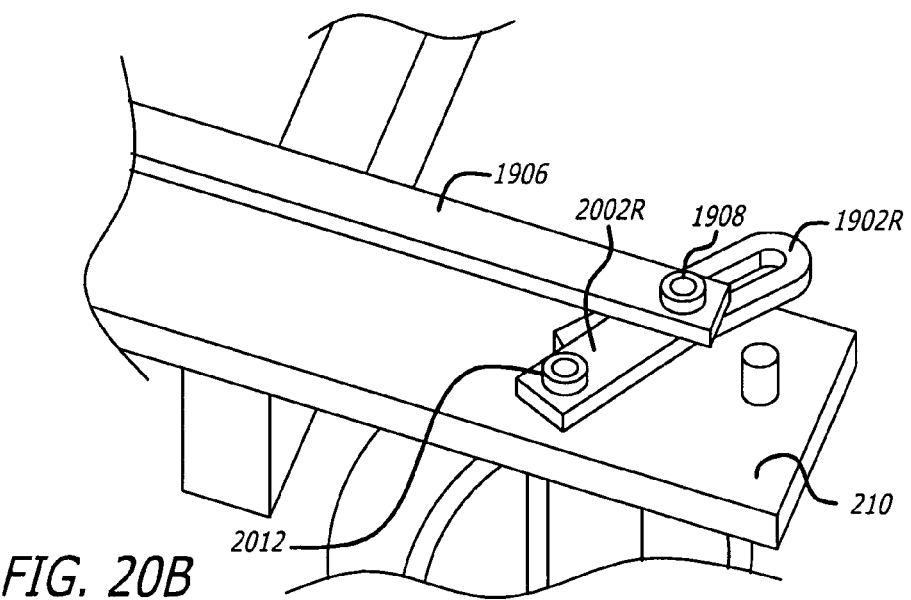
FIG. 20B illustrates a magnified perspective view of a portion of the steering system shown in FIG. 20A.

Referring now to FIGS. 19 and 20A-20B, a steering system 1900 is illustrated. The steering system 1900 is an alternate embodiment of the invention with elements above the steerable wheels 205L-205R. The steering system 1900 includes a pair of angled arms 1902L,1902R; a sliding bar 1906; and a tiller link 1920 moveably coupled together as shown.

As shown in FIG. 19, each of the angled arms 1902L, 1902R has a linear cam follower slot 1904. The left angled arm 1902L is coupled to the left steerable wheel 205L to pivot it about its axis 1210. The right angled arm 1902R is coupled to the right steerable wheel 205R to pivot it about its axis 1210.

The sliding bar 1906 has a pair of cam followers 1908 inserted into the pair of linear cam follower slots 1904 of the pair of angled arms 1902L,1902R. The sliding bar may further have a cam follower 1910 for insertion into a cam follower slot.

The tiller link 1920 has a linear cam follower slot 1922 over the cam follower 1910 in the sliding bar 1906. With respect to the chassis 210, the tiller link 1920 pivots about a pivot point 1924 near one end. The tiller link 1920 may coupled to the tiller 202 in various ways.

In a straight steering position, as is shown in FIG. 19, each of the pair of angled arms has an offset angle 1930 that allows the sliding bar 1906 to move a linear distance 1932 to pivot the steerable wheels. The linearly sliding bar 1906 actuates the pair of angled arms 1902L,1902R by way of the cam follower 1908 sliding within the cam follower slot 1904.

Referring now to FIGS. 20A-20B, the steering system 1900 may further have a pair of ground links 2002L,2002R to assure the sliding bar 1906 slides linearly. As show in FIGS. 20A-20B, each of the pair of ground links 2002L,2002R are spaced apart from each other. Near one end, each of the pair of ground links are pivotally coupled near opposing ends of the sliding bar 1906 at the cam followers 1908. Near an opposite end, each of the pair of ground links are pivotally coupled to the chassis 210 at spaced apart pivot points 2012

CONCLUSION

The embodiments of the invention are thus described. While embodiments of the invention were described with reference to a patient side cart of a robotic surgical system, the embodiments of the invention are not so limited as they are equally applicable to other heavy medical equipment requiring a steering system to move the equipment from one position to another.

It is to be understood that the exemplary embodiments described and shown in the accompanying drawings are merely illustrative of and not restrictive on the broad invention, and that the embodiments of the invention not be limited to the specific constructions and arrangements shown and described, since various other modifications may occur to those ordinarily skilled in the art. Rather, the embodiments of the invention should be construed according to the claims that follow below.

What is claimed is:

1. A method for steering mobile medical equipment having four wheels, the method comprising:
   supporting medical equipment with a base above a floor over which a left steerable wheel, a right steerable wheel, and a pair of front wheels roll;
   receiving an input steering angle other than zero;
   linearly sweeping a long link in response to the input steering angle,
   pivoting a pair of short links in response to the linearly sweeping of the long link;
   pivoting a pair of cam plates in response to the pivoting of the pair of short links;
   transferring the pivoting of one of the pair of cam plates to a left wheel assembly to position the left steerable wheel at a left wheel angle; and
   transferring the pivoting of another one of the pair of cam plates to a right wheel assembly to position the right steerable wheel at a right wheel angle.

2. The method of claim 1, further comprising
   pivoting a tiller link to receive the input steering angle.

3. The method of claim 2, wherein
   the pair of front wheels are motorized wheels and the method further comprises:
   driving the pair of motorized wheels to move the mobile medical equipment over the floor.

4. The method of claim 1, wherein
   the position of the right steerable wheel differs from the position of the left steerable wheel such that an axis of rotation of the pair of front wheels substantially intersects different axes of rotation of the right steerable wheel and the left steerable wheel at a center of turn to turn the mobile medical equipment over the floor substantially around the center of turn.

5. The method of claim 1, wherein
   the medical equipment is a patient side cart of a robotic surgical system including one or more robotic surgical arms.

6. The method of claim 1, wherein
   the first wheel angle of the first steerable wheel and the second wheel angle of the second steerable wheel are limited to provide a radius turn with a radius of not less than half a width of the base.

7. A method for steering mobile medical equipment having four wheels, the method comprising
    supporting medical equipment with a base above a floor over which a left steerable wheel, a right steerable wheel, and a pair of front motorized wheels roll;
    receiving an input steering angle other than zero;
    linearly sweeping a long link in response to the input steering angle,
    pivoting a pair of short links in response to the linearly sweeping of the long link;
    pivoting a pair of cam plates in response to the pivoting of the pair of short links;
    positioning the left steerable wheel with a left wheel assembly at a left wheel angle in response to the pivoting of one of the pair of cam plates;
    positioning the right steerable wheel with a right wheel assembly at a right wheel angle in response to the pivoting of another one of the pair of cam plates; and
    limiting the generating of the left wheel angle and the right wheel angle to avoid radius turns of substantially zero and avoid driving a first motorized wheel of the pair of front motorized wheels in one direction of rotation while concurrently driving a second motorized wheel of the pair of front motorized wheels in an opposite direction of rotation.

8. The method of claim 7, wherein
the limiting of the generating of the left wheel angle and the right wheel angle includes
    keeping the right steerable wheel and the left steerable wheel from pointing in opposite directions, wherein left and right are opposite directions.

9. The method of claim 8, wherein
the limiting of the generating of the left wheel angle and the right wheel angle includes
    keeping the right steerable wheel and the left steerable wheel pointing towards a similar direction.

10. The method of claim 9, wherein
the similar direction is left and
    the right steerable wheel and the left steerable wheel are kept pointing towards the left to avoid radius turns of substantially zero degrees.

11. The method of claim 9, wherein
the similar direction is right and
    the right steerable wheel and the left steerable wheel are kept pointing towards the right to avoid radius turns of substantially zero degrees.

12. The method of claim 7, wherein
the position of the right steerable wheel differs from the position of the left steerable wheel such that an axis of rotation of the pair of front wheels substantially intersects different axes of rotation of the right steerable wheel and the left steerable wheel at a center of turn to turn the mobile medical equipment over the floor substantially around the center of turn.

13. The method of claim 7, wherein
the medical equipment is a patient side cart of a robotic surgical system including one or more robotic surgical arms.

14. The method of claim 7, further comprising:
the pair of motorized wheels are spaced apart from each other.

15. The method of claim 14, further comprising:
driving a first motorized wheel of the pair of motorized wheels in a first direction of rotation with a first motor.

16. The method of claim 15, further comprising:
driving a second motorized wheel of the pair of motorized wheels in the first direction of rotation with a second motor; and
wherein the first and second motors are spaced apart from each other.

17. The method of claim 15, wherein the first and second motors are spaced apart from each other and the method further comprises:
    after driving the first motorized wheel, driving a second motorized wheel of the pair of motorized wheels in a second direction of rotation with a second motor opposite the first direction.

* * * * *